(12) United States Patent
Sauer

(10) Patent No.: US 11,064,990 B2
(45) Date of Patent: Jul. 20, 2021

(54) CARDIAC RETRACTOR

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 16/407,171

(22) Filed: May 8, 2019

(65) Prior Publication Data

US 2019/0343505 A1 Nov. 14, 2019

Related U.S. Application Data

(60) Provisional application No. 62/668,751, filed on May 8, 2018.

(51) Int. Cl.
*A61B 17/02* (2006.01)
*A61B 17/00* (2006.01)

(52) U.S. Cl.
CPC ...... *A61B 17/0218* (2013.01); *A61B 17/0206* (2013.01); *A61B 2017/00243* (2013.01); *A61B 2017/0237* (2013.01)

(58) Field of Classification Search
CPC ............ A61B 17/0218; A61B 17/0206; A61B 17/06114; A61B 17/0469; A61B 17/0482; A61B 2017/00243; A61B 2017/0237; A61B 2017/00477; A61B 2017/00407; A61B 2017/0225; A61B 2017/00398; A61B 2017/3427; A61B 2017/00862; A61B 2017/00685

USPC ................................................. 600/201–233
See application file for complete search history.

(56) References Cited

U.S. PATENT DOCUMENTS

| | | | |
|---|---|---|---|
| 6,394,951 B1 * | 5/2002 | Taylor .............. | A61B 17/00234 600/210 |
| 6,475,142 B1 * | 11/2002 | Parsons .............. | A61B 17/0206 600/228 |
| 6,592,573 B2 * | 7/2003 | Castaneda .......... | A61B 17/3417 604/164.04 |
| 6,651,671 B1 * | 11/2003 | Donlon ............ | A61B 17/00234 128/898 |
| 2010/0286485 A1 * | 11/2010 | Valentini .................. | A61B 1/32 600/224 |

* cited by examiner

*Primary Examiner* — Pedro Philogene
(74) *Attorney, Agent, or Firm* — Michael E. Coyne; Christopher B. Miller

(57) ABSTRACT

A cardiac retractor is disclosed. The cardiac retractor has an outer tube. The cardiac retractor also has a fixed collar fixedly coupled to a proximal end of the outer tube. The cardiac retractor further has a fixed link fixedly coupled to a distal end of the outer tube. The cardiac retractor also has an inner tube rotatable within the outer tube. The cardiac retractor further has a fixed key coupled to a proximal end of the inner tube and configured to rotate the inner tube relative to the outer tube. The cardiac retractor also has a keyed link coupled to a distal end of the outer tube.

6 Claims, 37 Drawing Sheets

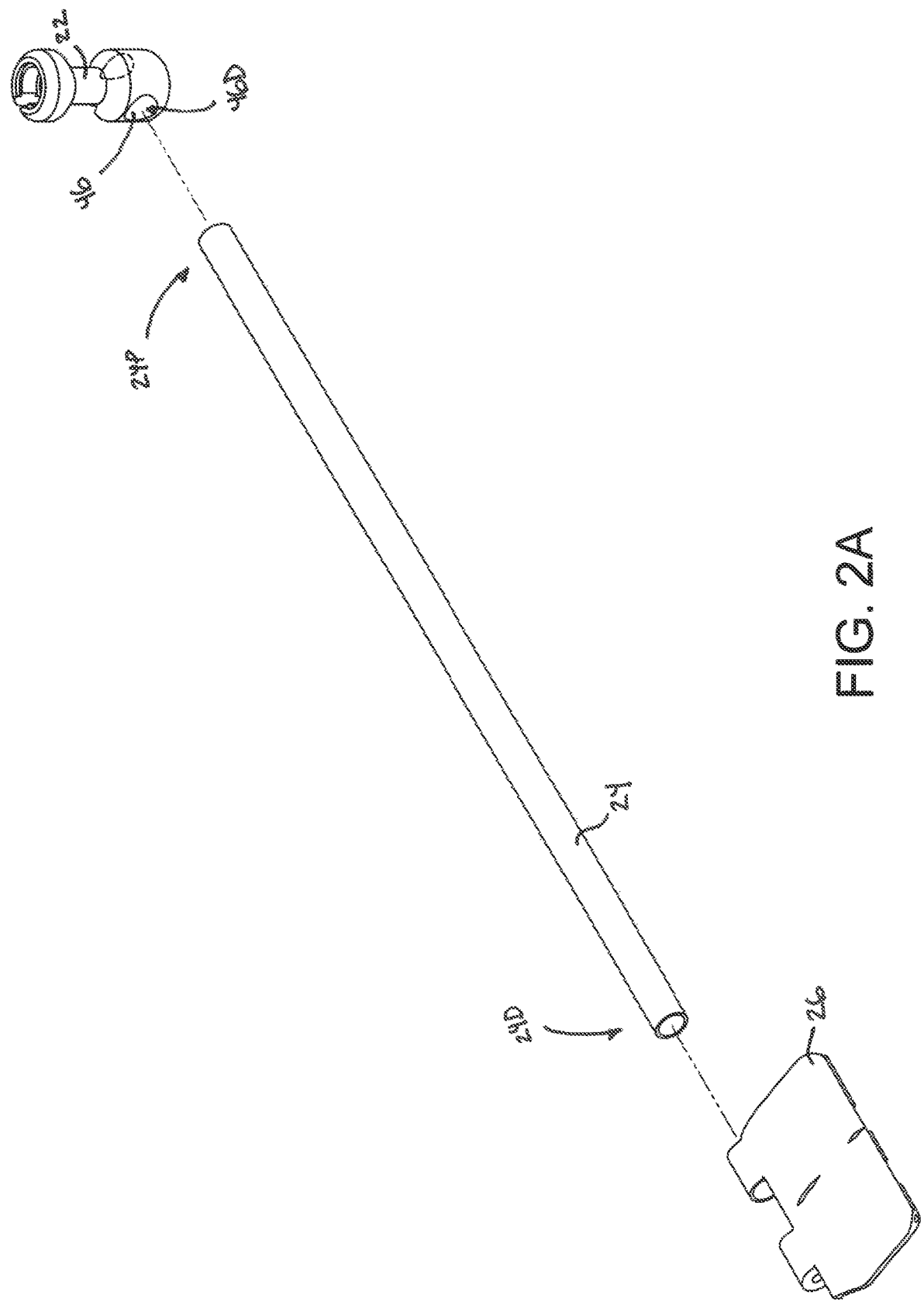

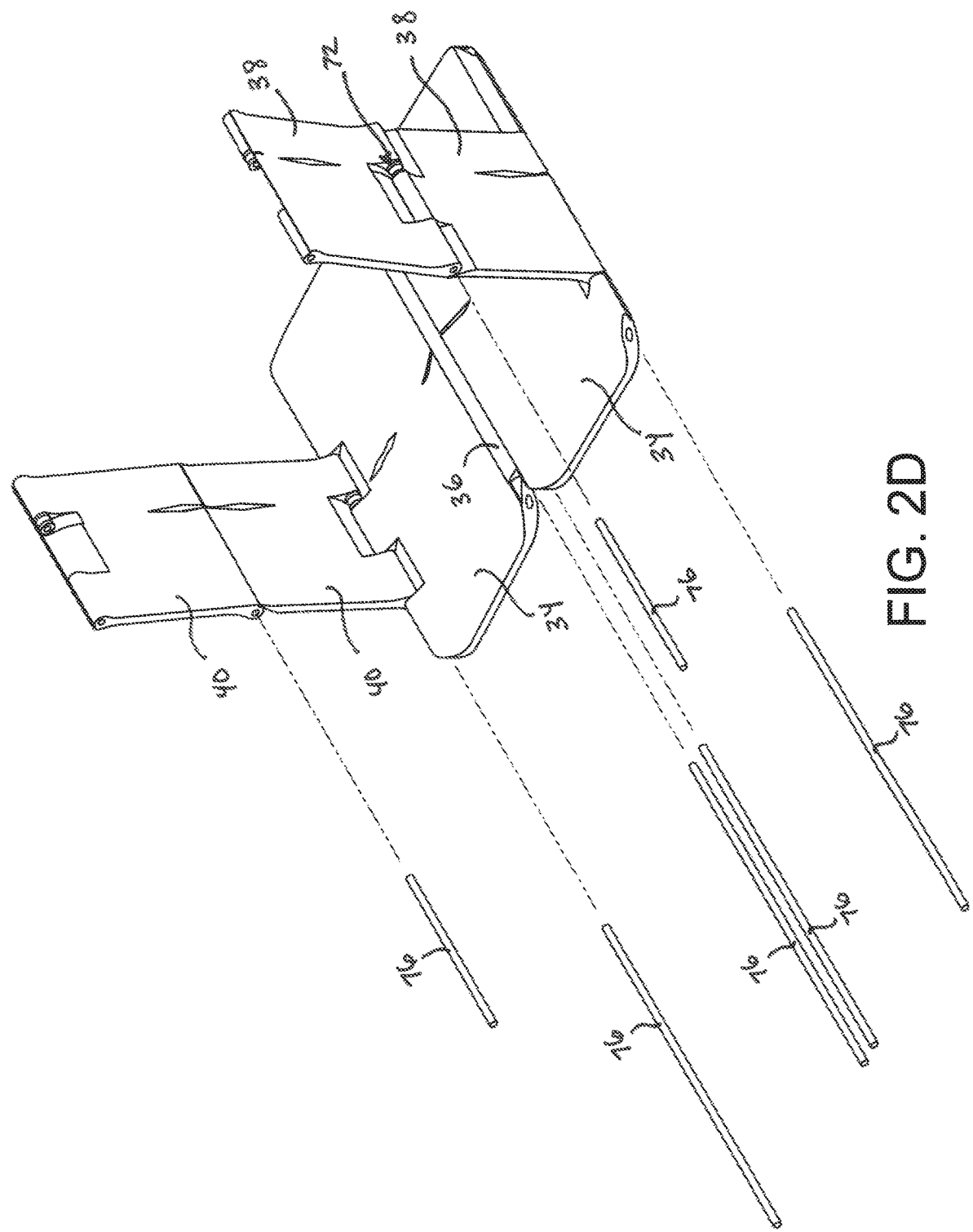

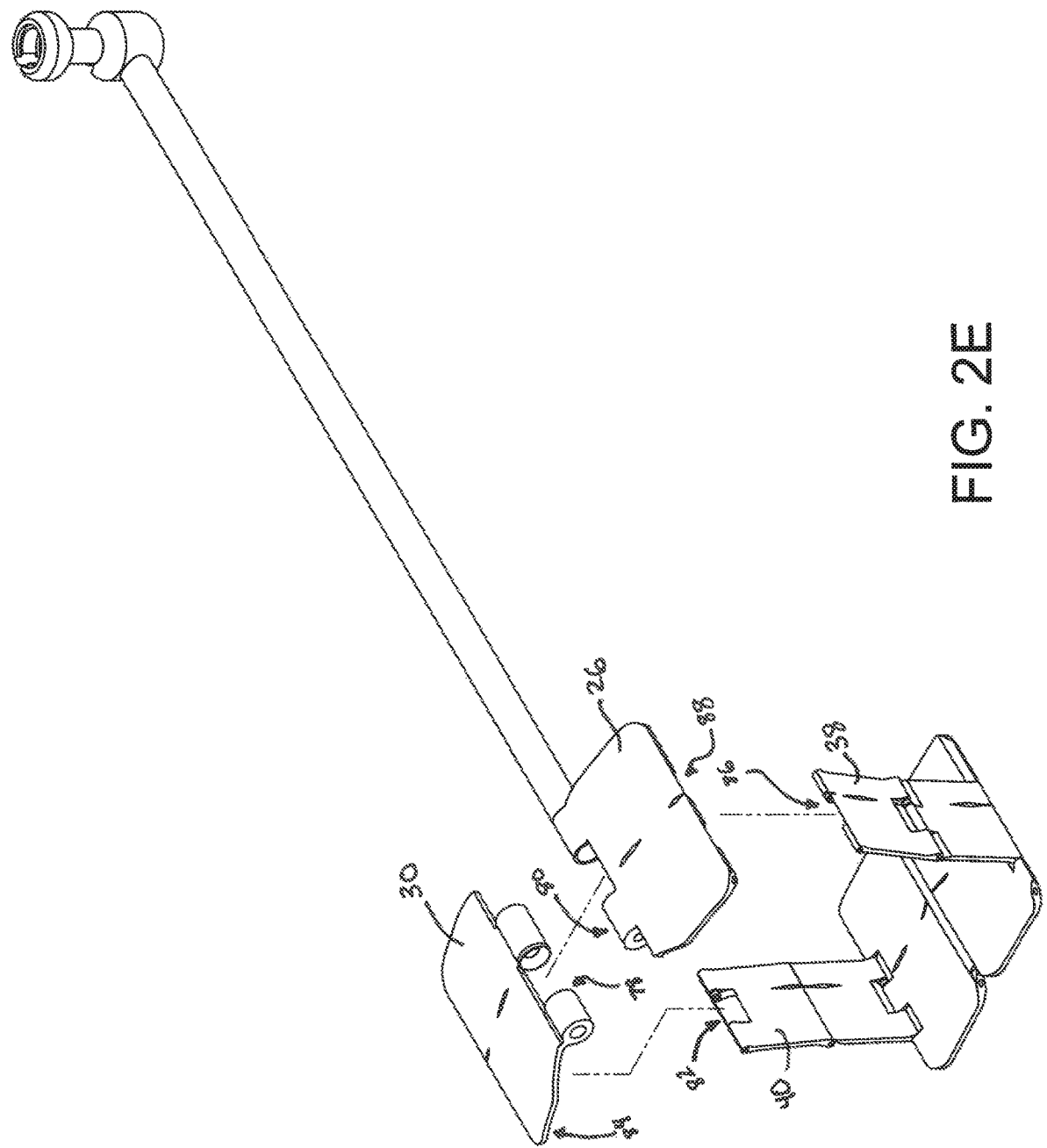

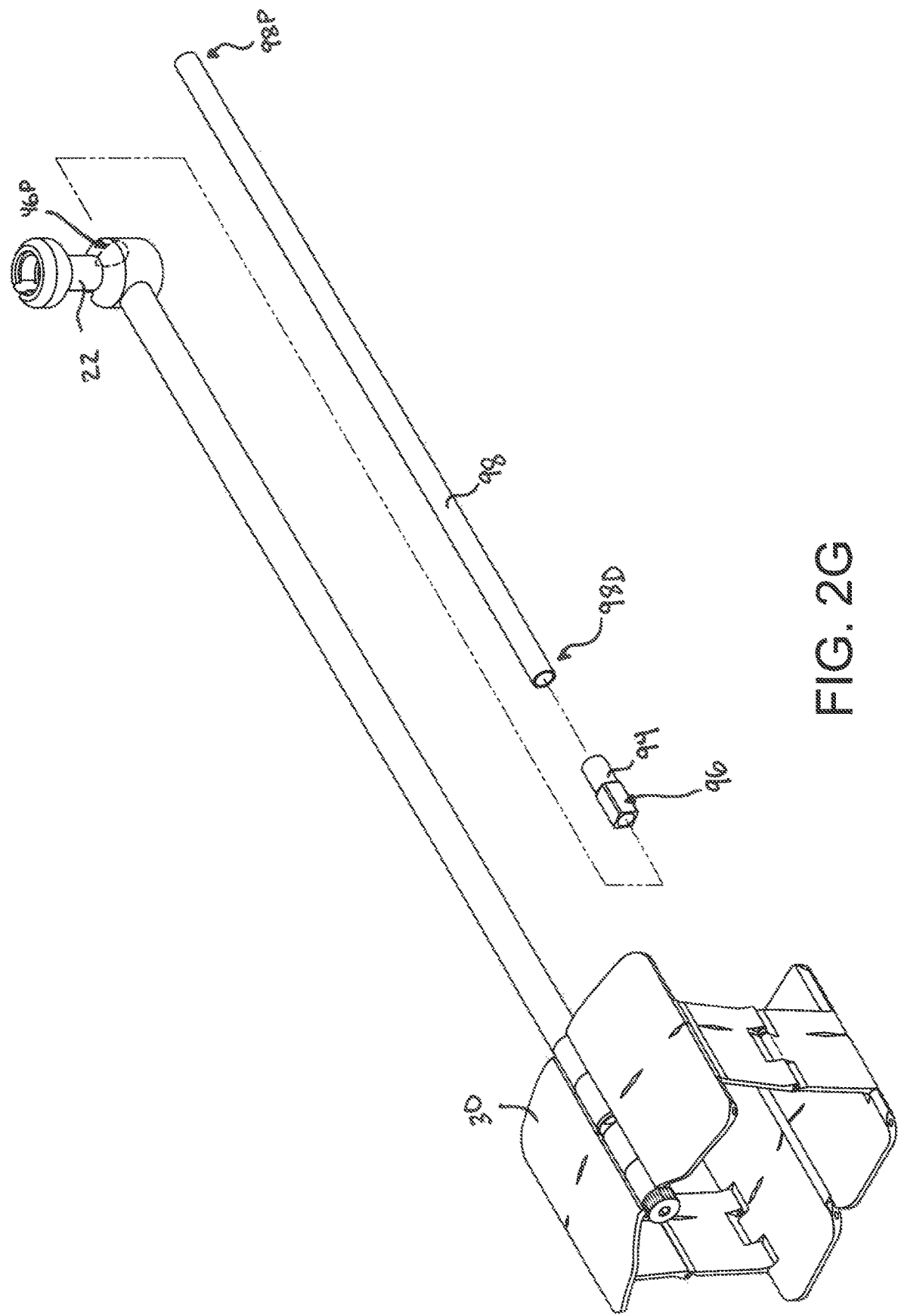

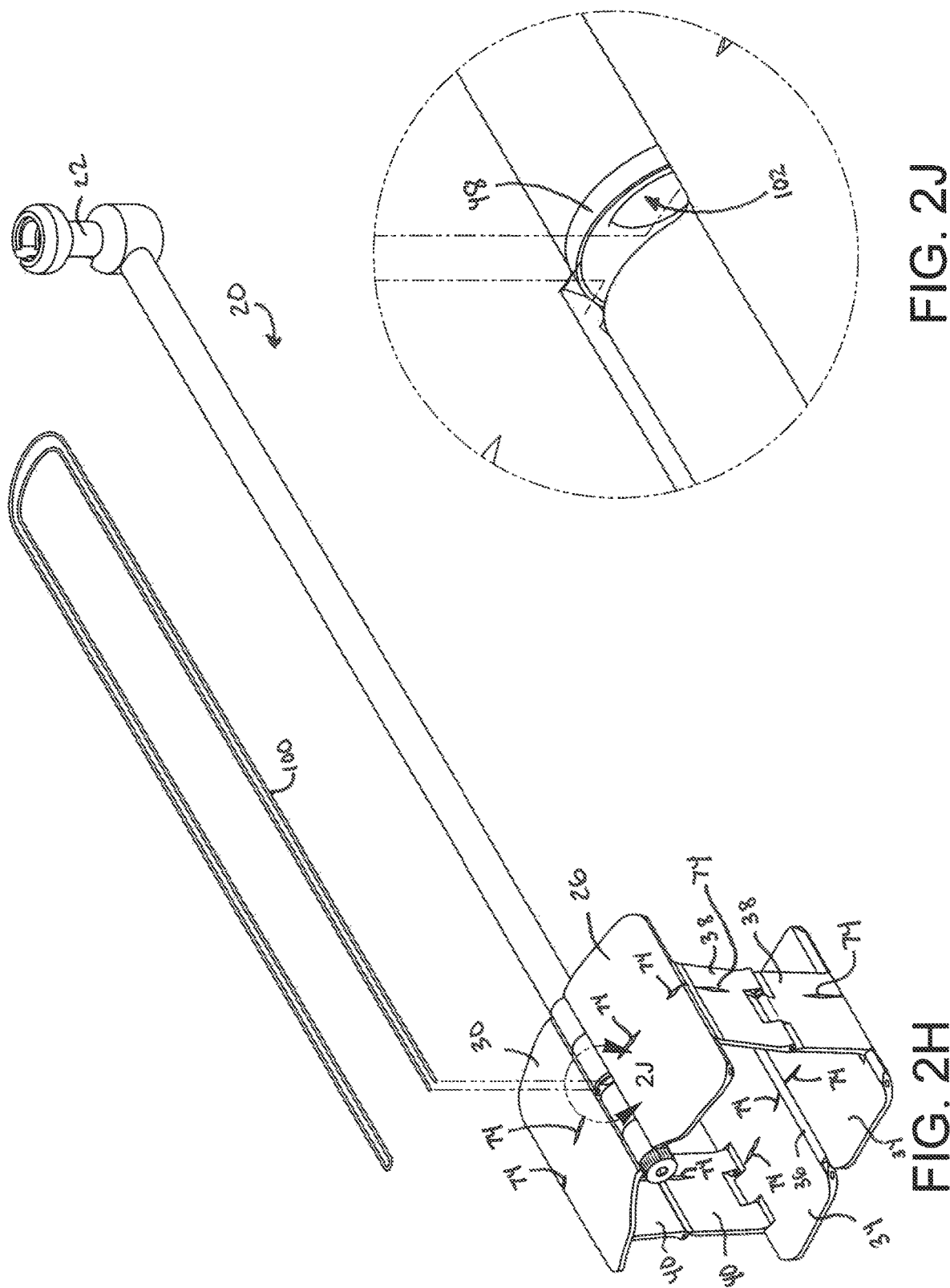

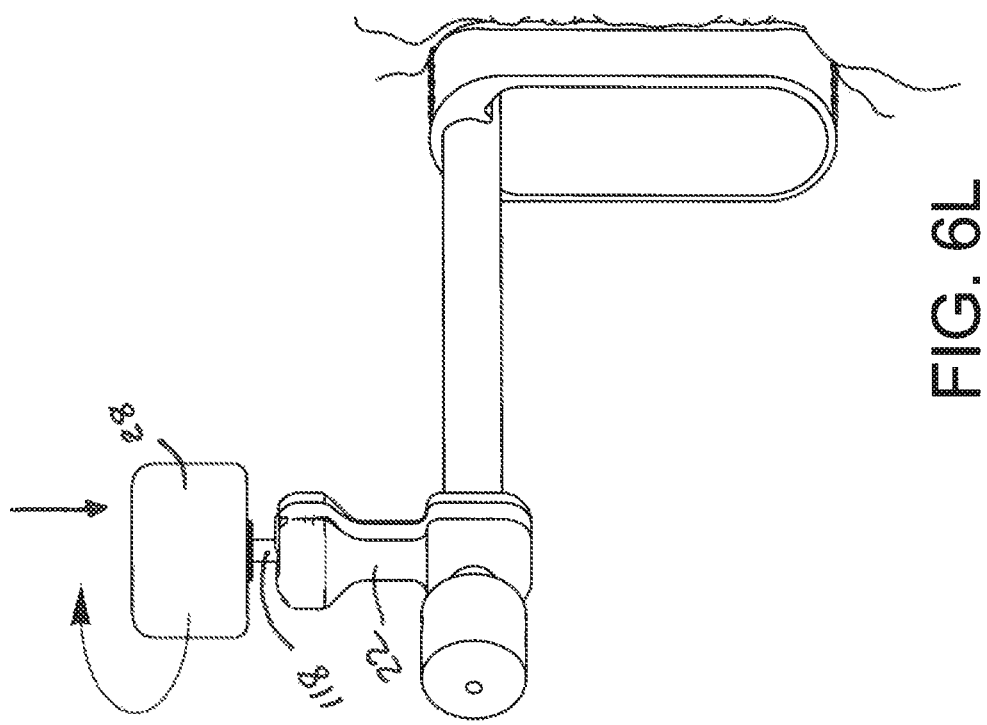
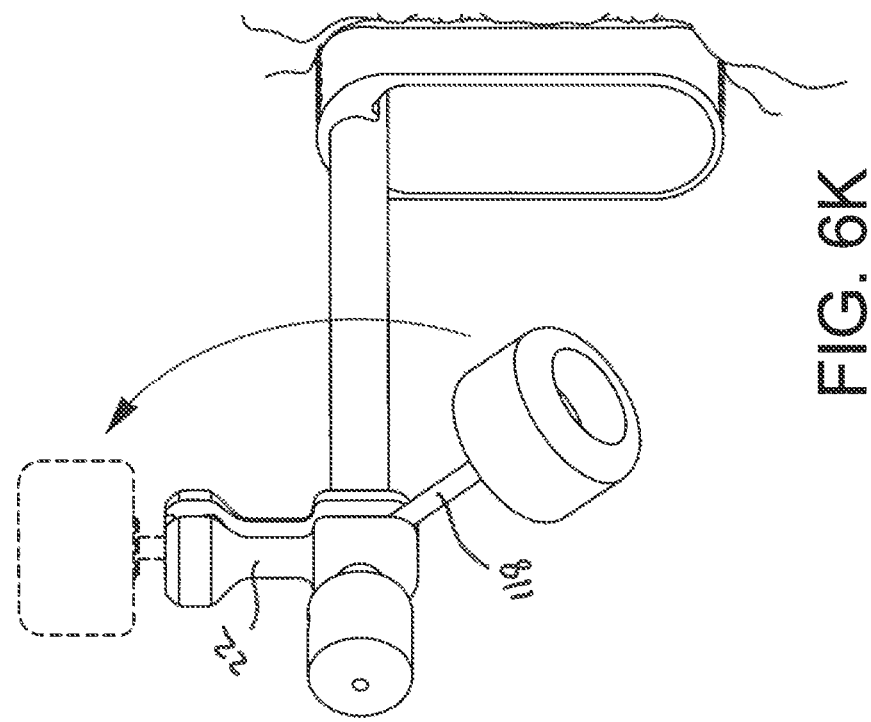

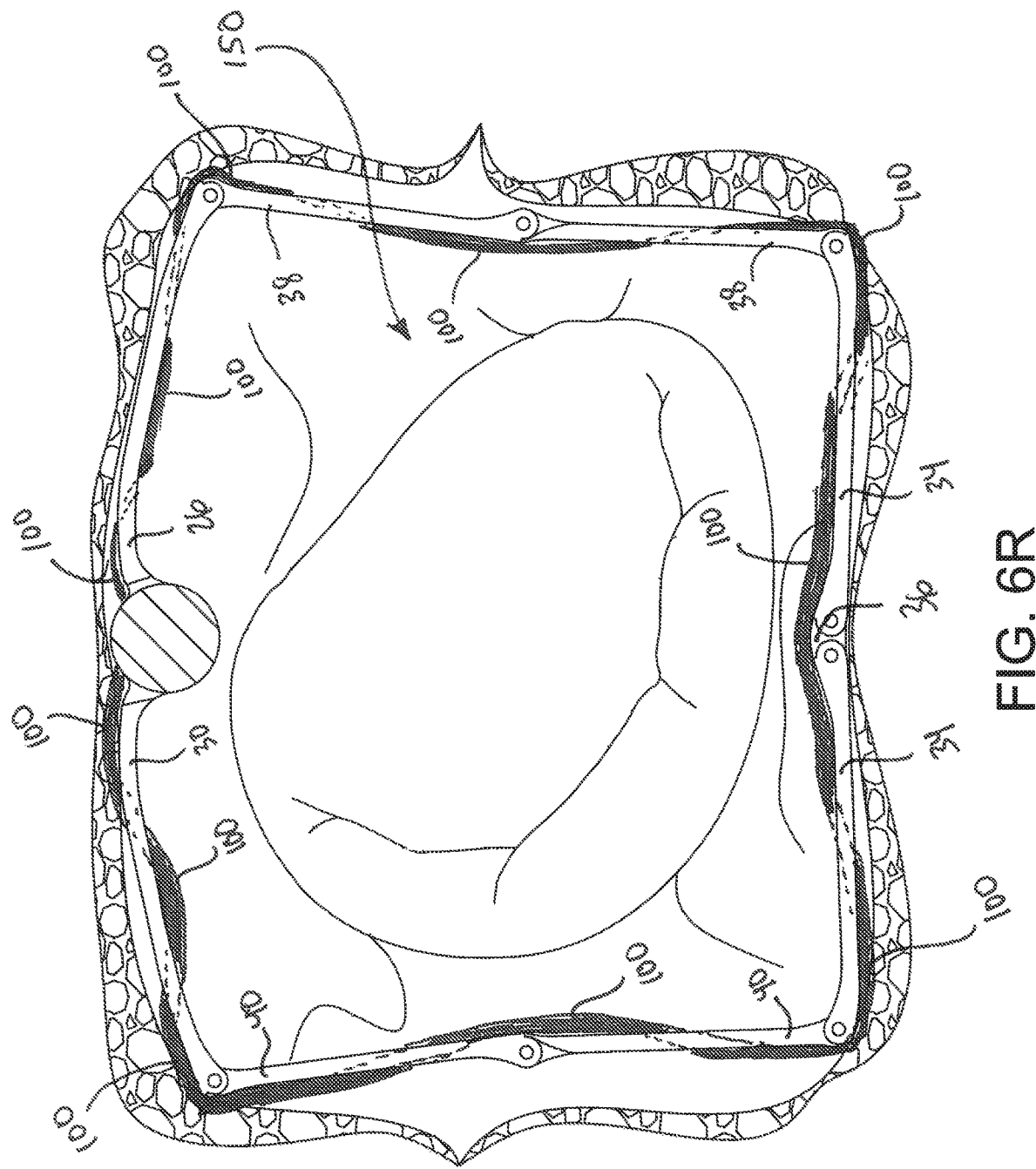

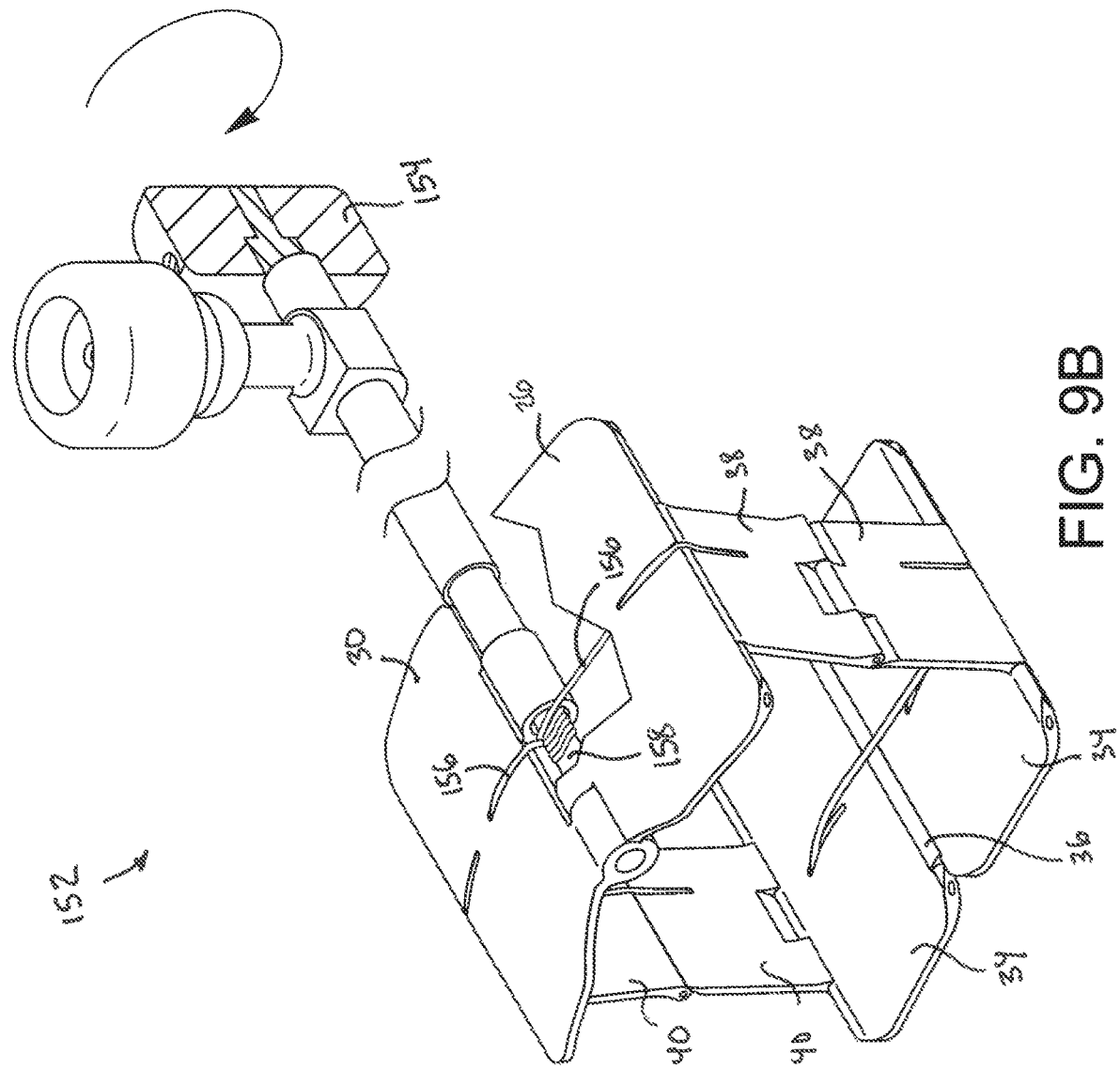

CARDIAC RETRACTOR

RELATED APPLICATION

This application claims priority to U.S. Provisional Patent Application No. 62/668,751, filed May 8, 2018 and entitled, "CARDIAC RETRACTOR". The 62/668,751 application is hereby incorporated by reference in its entirety.

FIELD

The claimed invention relates to surgical retractors, and more specifically to surgical retractors for use in minimally invasive cardiac surgery.

BACKGROUND

Modern advances in cardiac surgery have made it possible to repair or replace heart valves using minimally invasive surgical techniques. As minimally invasive techniques have improved, surgeons are able to operate on patients through smaller and smaller access incisions, resulting in less perioperative pain and shorter recovery times. Unfortunately, many cardiac retractors used in maintaining an opening in the wall of the heart require more than one access incision when used in minimally invasive surgery: one incision for the majority of the retractor to be passed through, and a second incision through which a manipulator/stabilizer is inserted to be coupled to the retractor to keep the retractor aligned as desired.

It would be desirable to have a reliable, simple to use cardiac retractor for use in minimally invasive surgery which could be deployed through a single minimally invasive incision/opening.

SUMMARY

A cardiac retractor is disclosed. The cardiac retractor has an outer tube. The cardiac retractor also has a fixed collar fixedly coupled to a proximal end of the outer tube. The cardiac retractor further has a fixed link fixedly coupled to a distal end of the outer tube. The cardiac retractor also has an inner tube rotatable within the outer tube. The cardiac retractor further has a fixed key coupled to a proximal end of the inner tube and configured to rotate the inner tube relative to the outer tube. The cardiac retractor also has a keyed link coupled to a distal end of the outer tube.

BRIEF DESCRIPTION OF THE DRAWINGS

FIGS. 2A-2H and 2J are a series of exploded perspective views which illustrate the partial assembly of the cardiac retractor of FIG. 1. It should be noted that there is intentionally not a FIG. 2I to avoid confusion with the number 21.

FIGS. 6A-6H, 6J-6N, and 6P-6R illustrate an example of a surgical procedure using the cardiac retractor of FIG. 1 and the keyhole cannula of FIG. 4.

FIGS. 9A and 9B are both partial cross-sectional and partially exposed views which illustrate the deployment cable mechanism for the cardiac retractor embodiment of FIG. 7.

Figure 1:
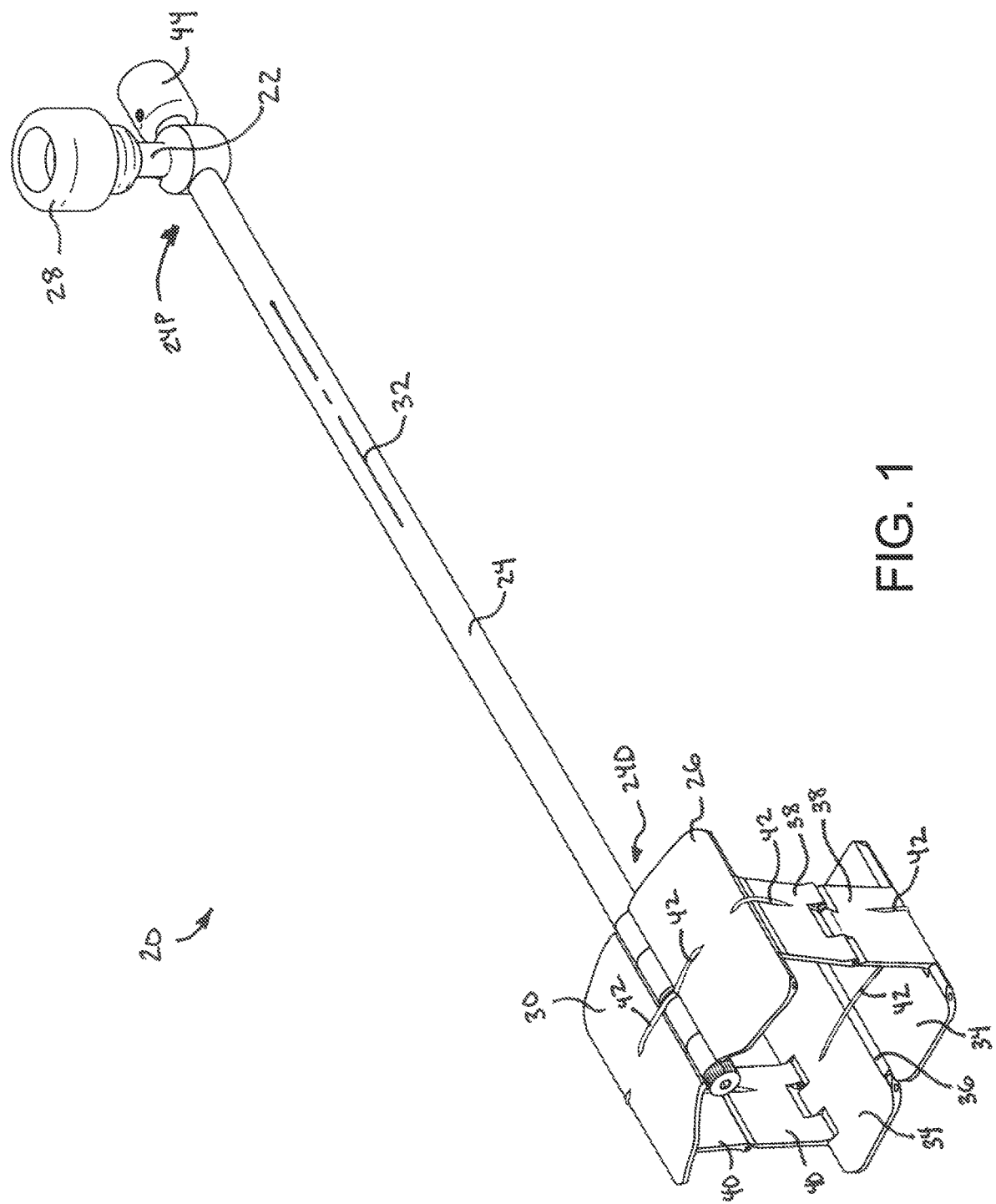
FIG. 1 is a perspective view of one embodiment of a cardiac retractor.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 illustrates one embodiment of a cardiac retractor 20. The retractor has a fixed collar 22 which is fixedly attached to the proximal end 24P of an outer tube 24. A fixed link 26 is fixedly attached to the distal end 24D of the outer tube 24. A coaxial nut 28 is coupled to a keyed link 30 by elements which are not visible in this view, but which will be shown and discussed later in this specification. The coaxial nut 28 is coupled to a fixed key (not visible in this view) which can be rotated around an axis 32 of the outer tube 24 to cause a related movement of the keyed link 30. As shown in FIG. 1, the with the coaxial nut 28 aligned over the fixed collar 22, the keyed link 30 is opened or deployed relative to the fixed link 26.

In this embodiment, the cardiac retractor 20 has a series of additional links in addition to the fixed link 26 and the keyed link 30. Two opposing links 34 are located opposite the keyed link 30 and the fixed link 26. The opposing links 34 are coupled together by a coupling link 36. A first opposing link 34 is coupled to the fixed link 26 by two side links 38, while a second opposing link 34 is coupled to the keyed link 30 by two side links 40. Each link in a pair of adjacent links (30/40, 40/40, 40/34, 34/36, 36/34, 34/38, 38/26) is pivotable relative to each other. A deployment cable 42 is routed around the links 26, 38, 38, 34, 36, 34, 40, 40, 30 in a pattern which will cause the links to open into the deployed state shown in FIG. 1 when tension is applied to the deployment cable 42 by a cable tension screw knob 44.

Figure 2B:
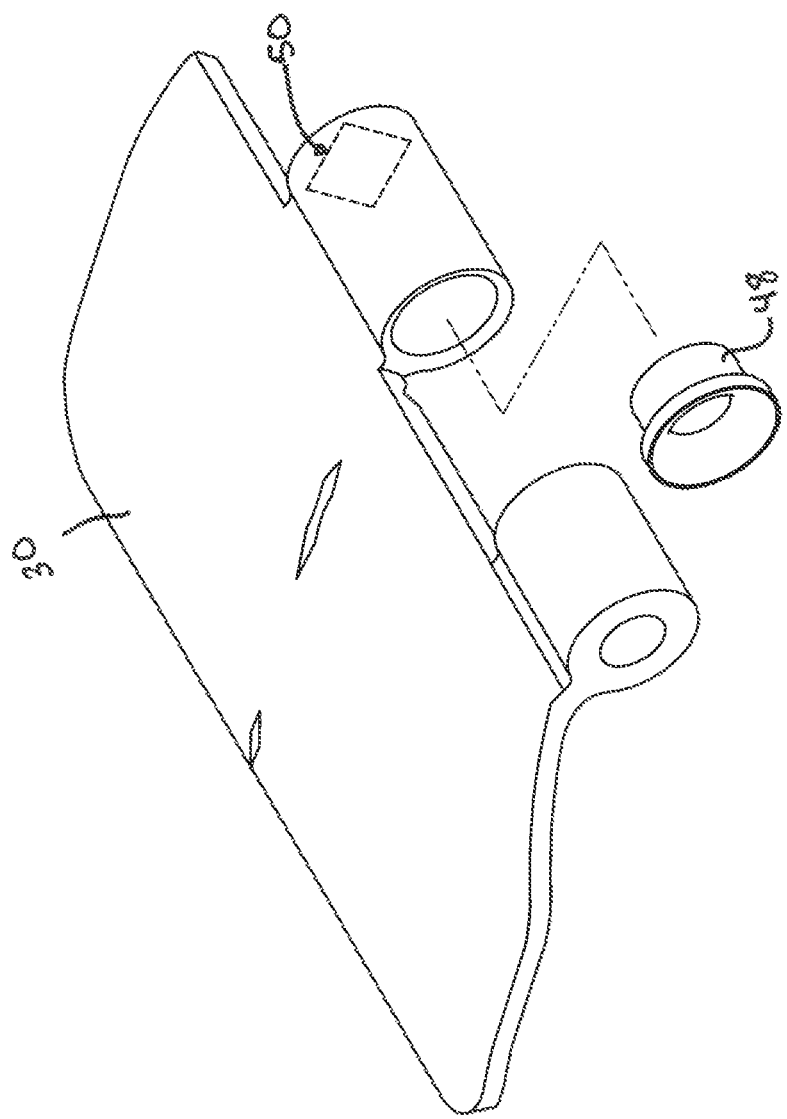

FIGS. 2A-2H and 2J are a series of exploded perspective views which illustrate the partial assembly of the cardiac retractor of FIG. 1. It should be noted that there is intentionally not a FIG. 2I to avoid confusion with the number 21. As shown in FIG. 2A, the outer tube 24 is coupled to the fixed link 26 at the distal end 24D of the outer tube 24. The proximal end 24P of the outer tube 24 is coupled to the fixed collar at a distal side 46D of a passthrough hole 46 in the fixed collar 22.

Figure 2C:
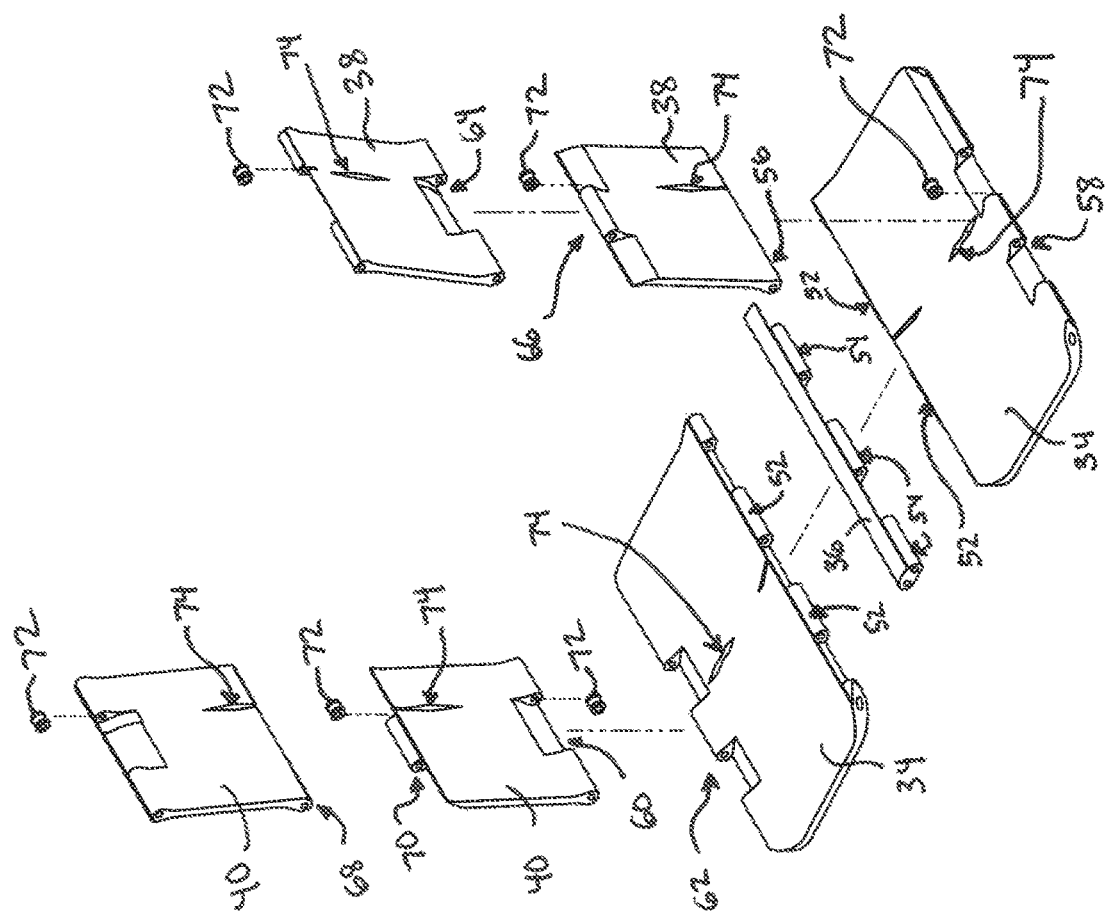

As shown in FIG. 2B, a cable bushing 48 is coupled to the keyed link 30. The keyed link 30 has a keyed opening 50 to which reference will be made in a later figure. As shown in FIG. 2C, hinges 52 of the opposing links 34 are aligned with corresponding hinges 54 of the coupling link 36. Similarly, hinge 56 of one of the side links 38 is aligned with corresponding hinge 58 of the first opposing link 34, while hinge 60 of one of the side links 40 is aligned with corresponding hinge 62 of the second opposing link 34. Also similarly, hinge 64 of another of the side links 38 is aligned with hinge 66 of the other side link 38, while hinge 68 of another of the side links 40 is aligned with the hinge 70 of the other side link 40. A series of side rollers 72 is aligned with a hinge on each of the links 38, 40, 34. The side rollers 72 line up with cable guide slots 74 in the links. As shown in FIG. 2D, a series of hinge pins 76 is used to hold each of the hinged joints between links 38, 40, 34 together, including the side rollers 72.

Figure 2F:
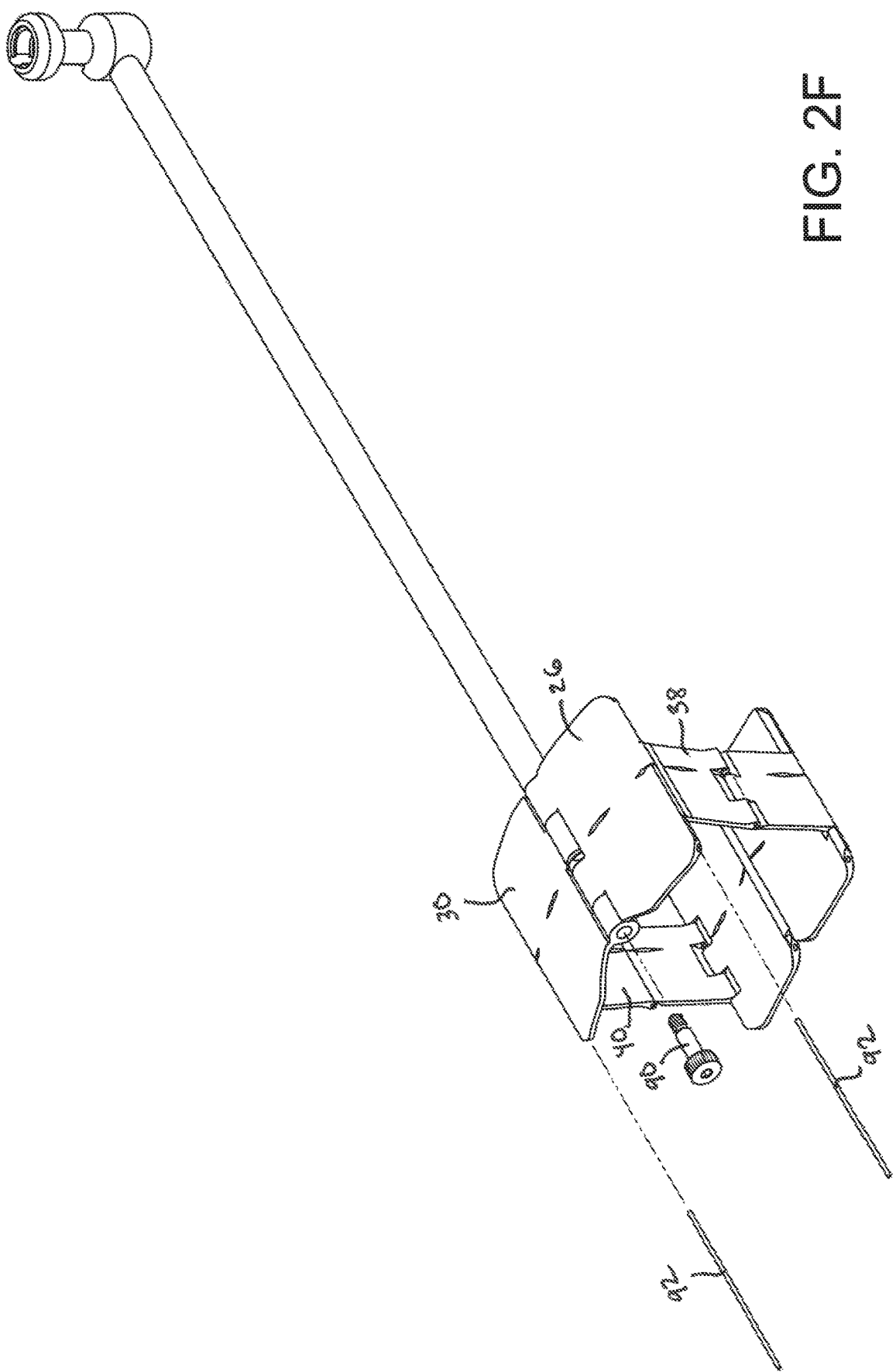

As shown in FIG. 2E, a hinge 78 of the keyed link 30 is brought into alignment with a hinge 80 of the fixed link 26. A hinge 82 of the side link 40 on one end is aligned with a hinge 84 of the keyed link 30. Similarly, a hinge 86 of the side link 38 on another end is aligned with a hinge 88 of the fixed link 26. As shown in FIG. 2F, the keyed link 30 is held pivotably coupled to the fixed link 26 by a threaded axle 90 which passed through the end of the keyed link 30 and screws into the fixed link 26. Hinge pins 92 are used to pivotably couple the keyed link 30 and fixed link 26 to their respective side links 40, 38.

As shown in FIG. 2G, a tube drive 94 having a keyed end 96 is coupled to the distal end 98D of an inner tube 98. The assembled tube drive 94 and inner tube 98 are then inserted into the proximal side 46P of a passthrough hole 46 in the fixed collar 22 until the keyed end 96 of the tube drive 94 engages the keyed opening 50 (visible in FIG. 2B) of the keyed link 30.

Figure 2K:
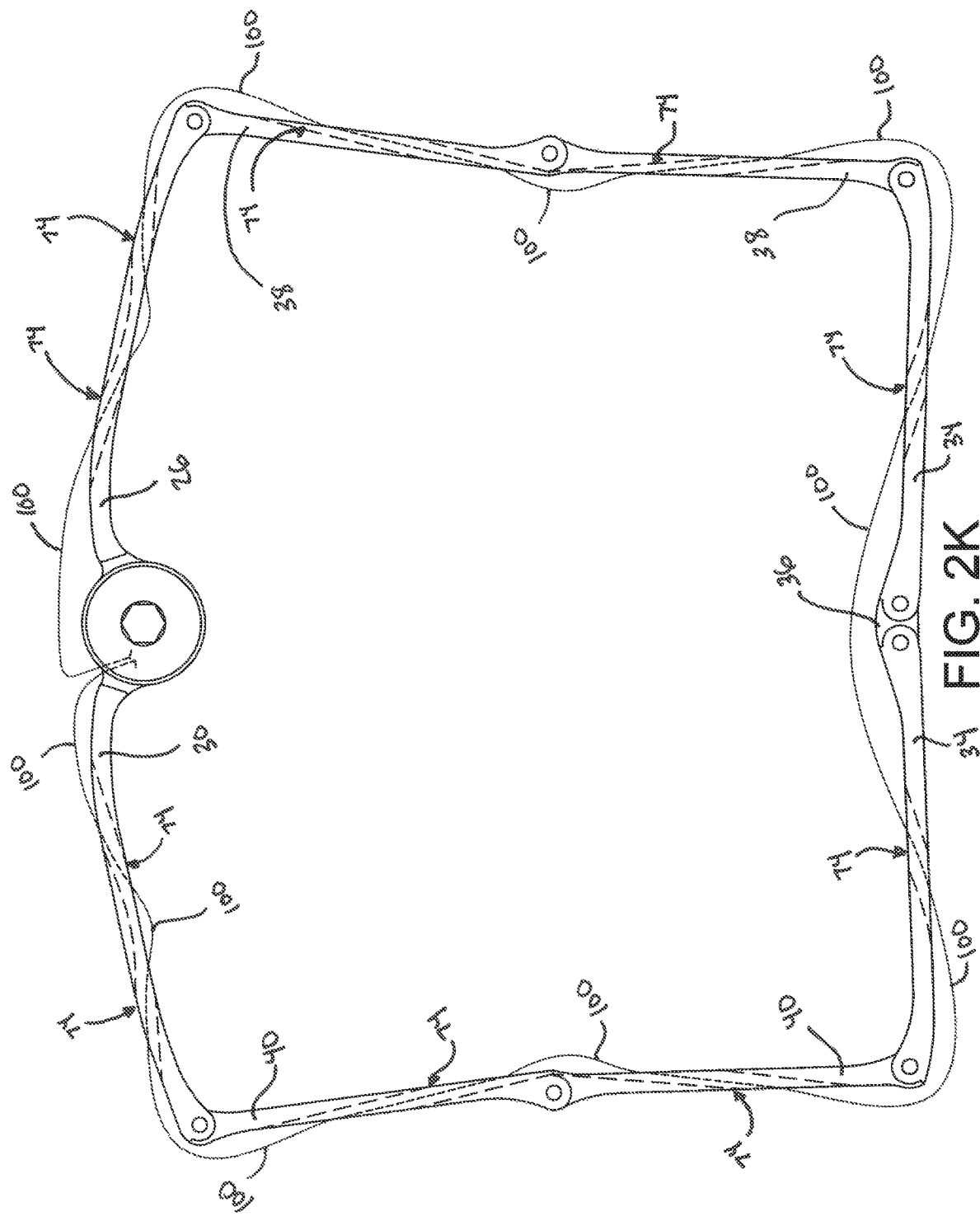
FIG. 2K is a schematic elevational view of an embodiment of the deployment cable routing for the assembly of the cardiac retractor of FIG. 1.

As shown in FIG. 2H, a deployment cable 100 is added to the cardiac retractor 20. The deployment cable 100 is routed around the links 26, 38, 38, 34, 36, 34, 40, 40, 30 as shown in the side view of FIG. 2K. FIG. 2J is an enlarged view of a portion of FIG. 2H, which shows an opening 102 in the cable bushing 48. After routing the deployment cable 100 around the links as shown in FIG. 2K, the ends of the deployment cable 100 are passed through the opening 102 in the cable bushing 48, passed down through the inner tube 98 (previously visible in FIG. 2G), and out of the opening 46P in the fixed collar 22 (also previously visible in FIG. 2G).

Figure 2L:
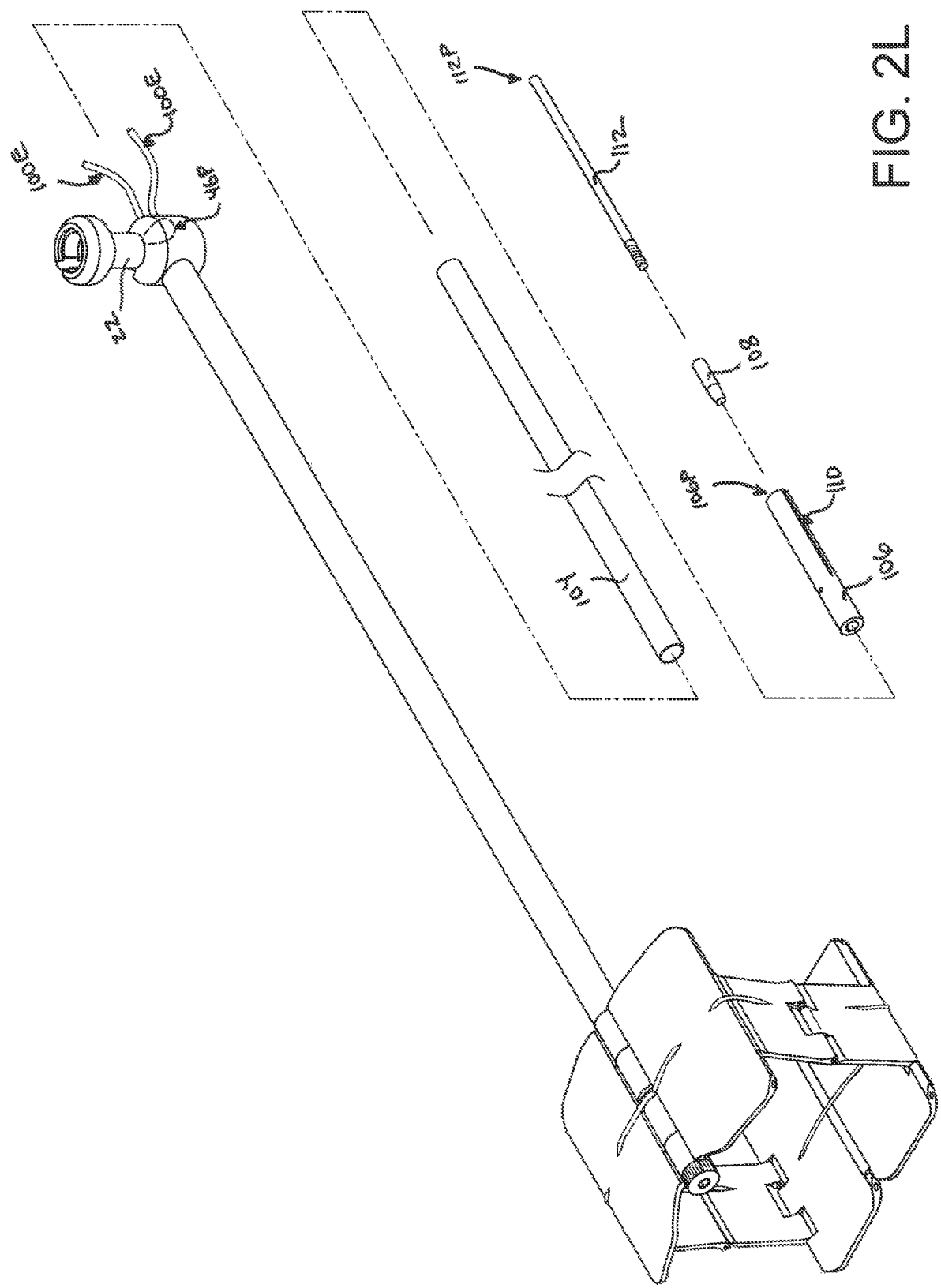
FIGS. 2L-2N are a continued series of exploded perspective views which illustrate the remaining assembly of the cardiac retractor of FIG. 1.

The ends 100E if the deployment cable 100 are shown exiting the opening 46P in FIG. 2L. An assembly spacer 104 (also known as a cable tube) is placed over the deployment cable ends 100E and into the opening 46P and slide inside the inner tube 98 (previously visible in FIG. 2G). A tension nut 106 is also placed over the deployment cable ends 100E and into the opening 46P to slide against the assembly spacer 104. A cable lock wedge 108 is pressed into the proximal end 106P of the tension nut 106, pinning the deployment cable 100 within the tension nut 106 while forcing the deployment cable ends 100E into slots 110 in the tension nut 106. Excess cable ends 100E are then trimmed at the tension nut 106. A threaded rod 112 is then threaded into the tension nut 106.

Figure 2M:
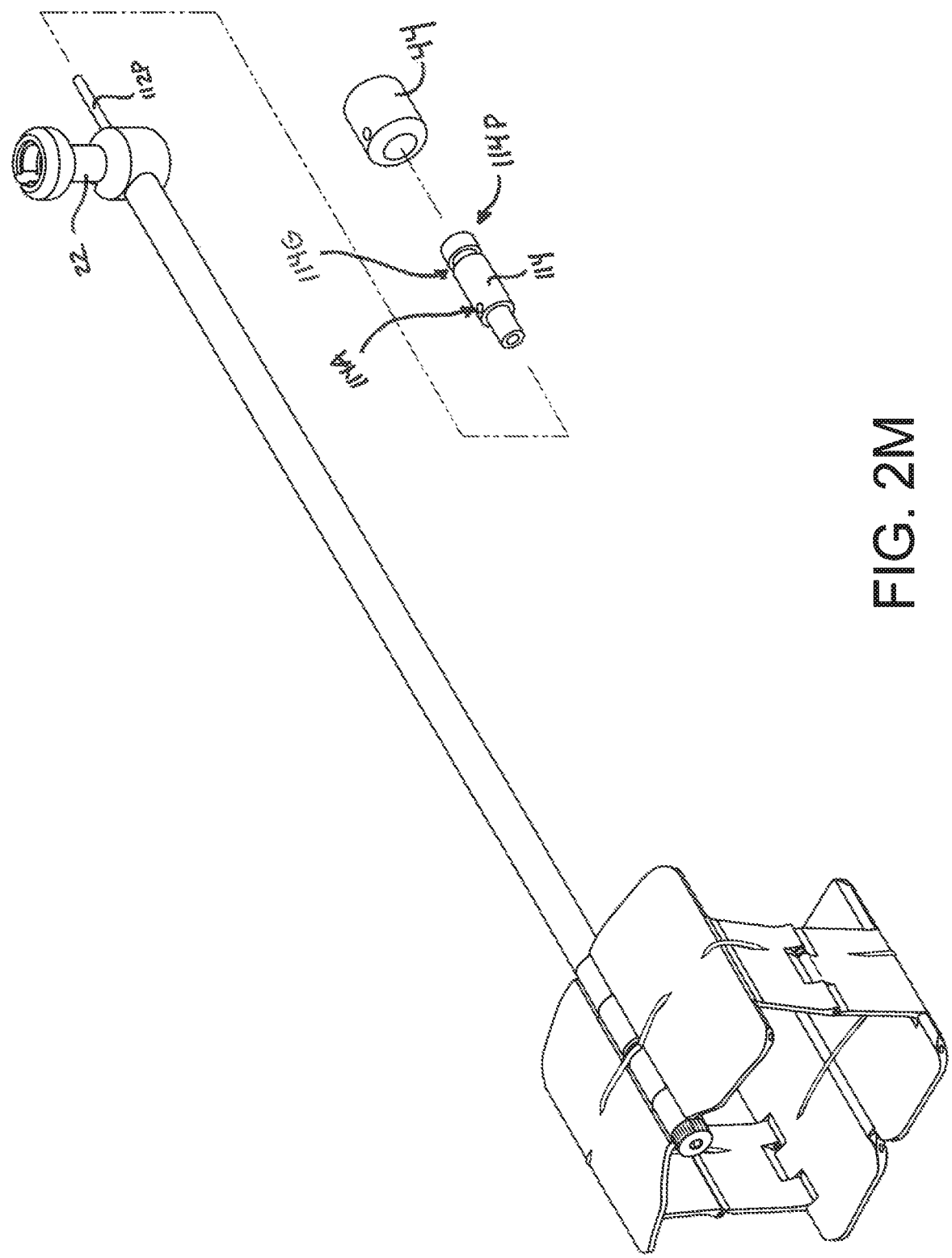

As shown in FIG. 2M, the proximal end 112P of threaded rod 112 protrudes from the fixed collar 22. A key mount collar 114 is passed over the proximal end 112P of threaded rod 112 and coupled to the inner tube 98 (previously visible in FIG. 2G). In the view of FIG. 2M, we also call out the attachment hole 114A and the groove 114G of key mount collar 114, since both will be referred to in the following figure. The cable tension screw knob 44 is then placed over the proximal end 114P of the key mount collar 114 while also being fixedly coupled to the proximal end 112P of threaded rod 112.

Figure 2N:
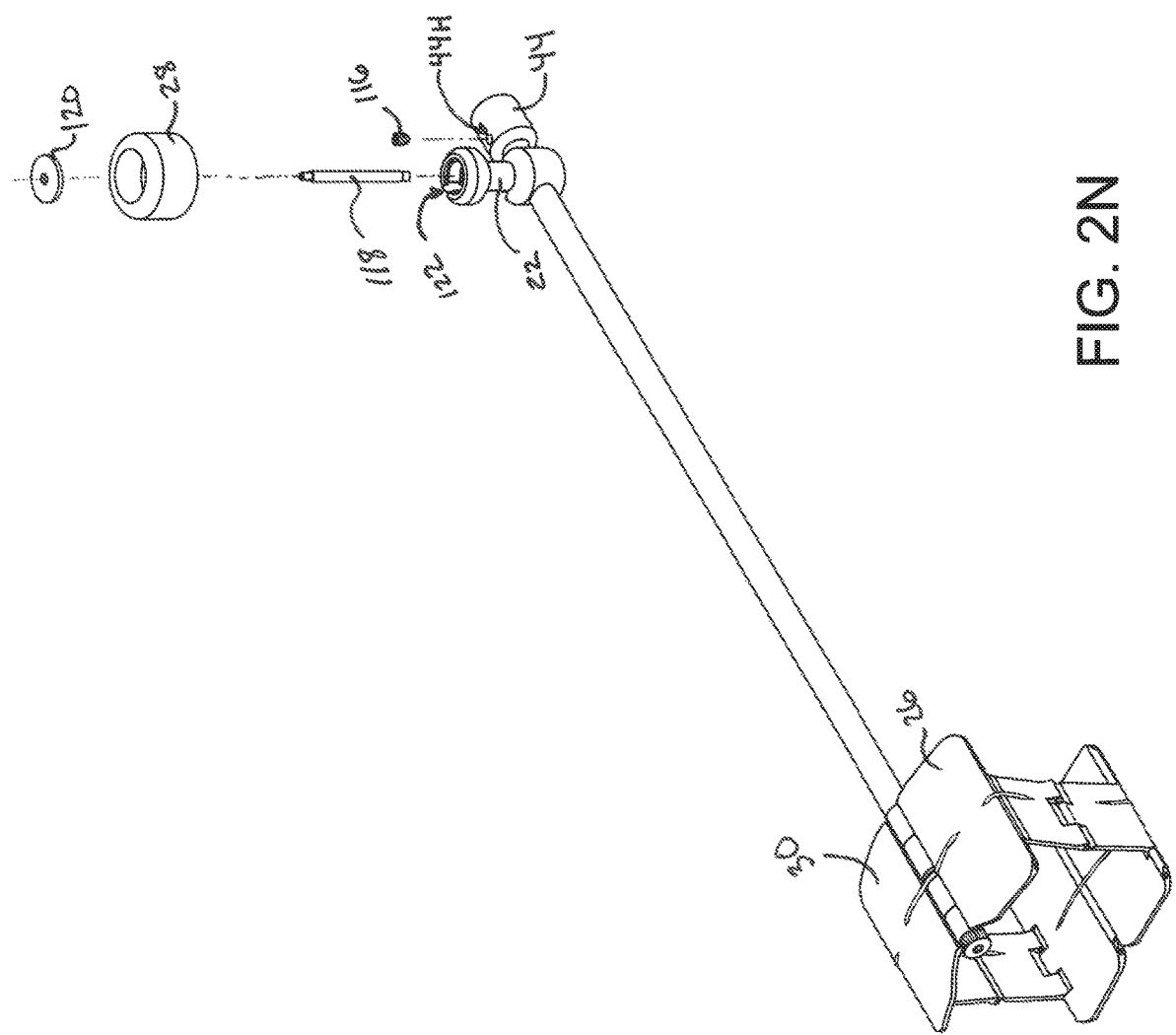

As shown in FIG. 2N, a set screw 116 is threaded into hole 44H of the cable tension screw knob 44 so that the set screw 116 also rides in the groove 114G of the key mount collar 114 (previously visible in FIG. 2M). A fixed key 118 is passed through the fixed collar 22 and coupled to the attachment hole 114A of the key mount collar 114. The coaxial nut 28 is slid over the fixed key 118, while a retaining washer 120 is coupled to the end of the fixed key 28 in order to keep the coaxial nut 28 from coming off the fixed key 118. The fixed collar 22 has a slot 122 which is sized to allow the fixed key 118 to be rotated out of the fixed collar 22 when the coaxial nut 28 is not threaded onto the fixed collar 22. Rotating the fixed key 118, rotates the key mount collar 114 to which it is connected, which in turn rotates the inner tube 98 (previously visible in FIG. 2G) to which it is connected, which in turn rotates the tube drive 94, which in turn rotates the keyed link 30 to which it is connected. When the fixed key 118 is aligned with the fixed collar 22, the keyed link 30 is in the open or deployed position shown in FIG. 2N. When the fixed key 118 is rotated out of the fixed collar 22, the keyed link 30 pivots towards the fixed link 26 for a closed or undeployed position (not shown in this view).

Figure 3A:
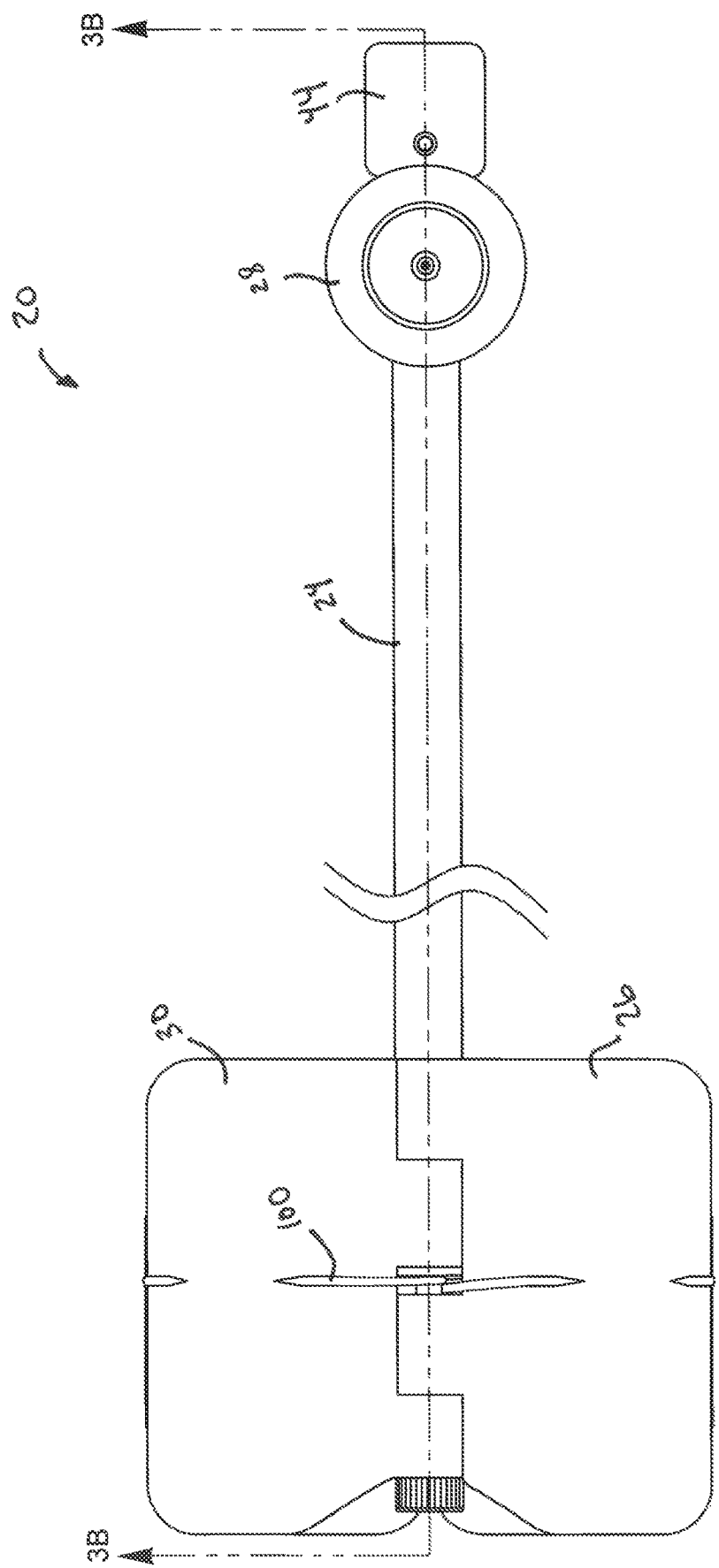
FIG. 3A is a top view of the cardiac retractor of FIG. 1 showing cross-section line 3B-3B.
Figure 3B:
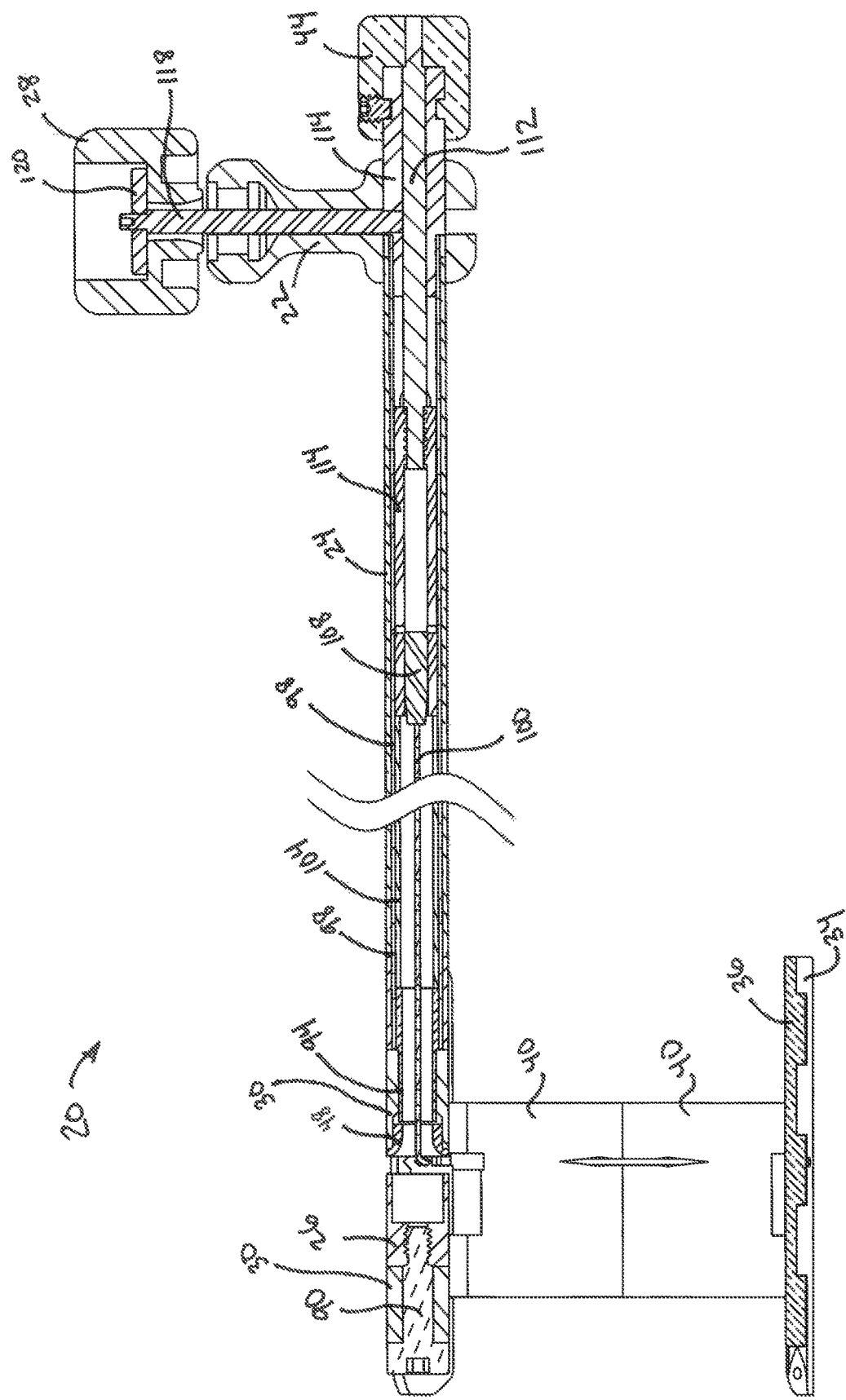
FIG. 3B is a side cross-sectional view of the cardiac retractor of FIG. 3A.

FIG. 3A is a top view of the cardiac retractor 20 of FIG. 1 showing cross-section line 3B-3B. FIG. 3B is a side cross-sectional view of the cardiac retractor 20 of FIG. 3A.

Figure 4:
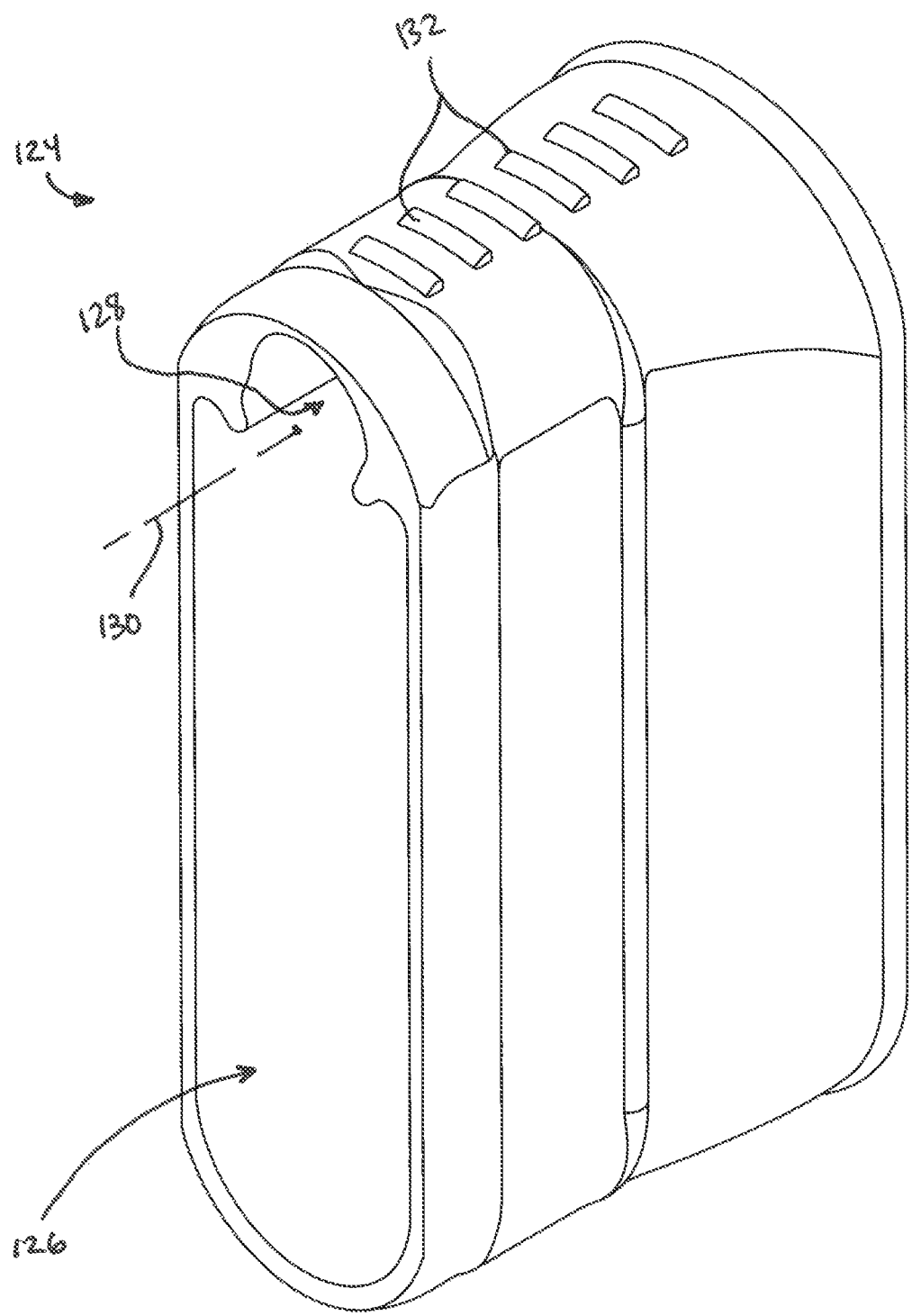
FIG. 4 is a perspective view of one embodiment of a keyhole cannula for use with a cardiac retractor such as the retractor of FIG. 1.
Figure 5D:
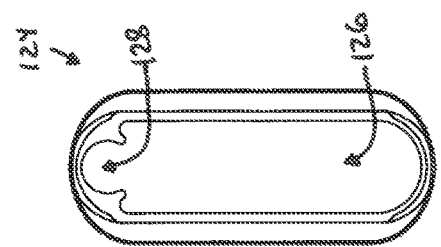
FIGS. 5A, 5B, 5C, 5D, 5E, and 5F are front, left, right, back, top, and bottom views, respectively, of the keyhole cannula of FIG. 4.
Figure 5C:
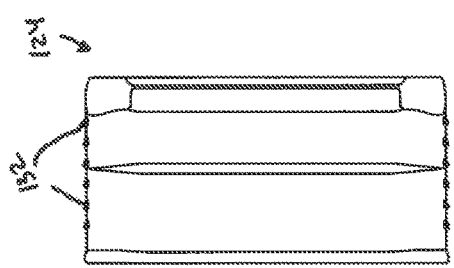
Figure 5E:
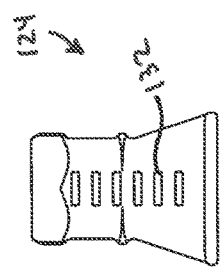
Figure 5A:
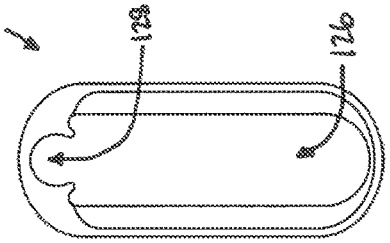
Figure 5F:
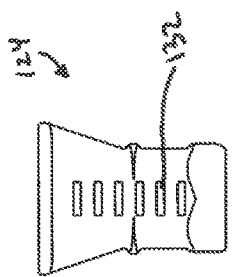
Figure 5B:
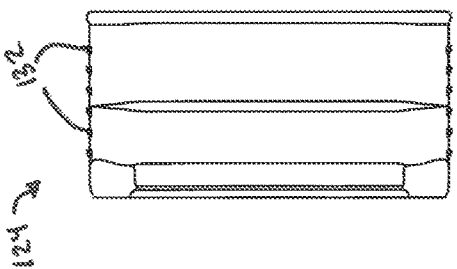

FIG. 4 is a distal perspective view of one embodiment of a keyhole cannula 124 for use with a cardiac retractor 20 such as the retractor of FIG. 1. The keyhole cannula 124 has an instrument passage 126 which in this embodiment is oblong in shape. Coupled to the instrument passage 126 is a key hole 128 which is sized to accept the outer tube 24 of the cardiac retractor 20 such that the device may only be slid into the key hole 128 along a key hole axis 130 which is substantially perpendicular to the opening of the passage 126. To accomplish this, the key hole 128 covers an arc of more than 180 degrees, thereby preventing a tube large enough to fill the whole key hole 128 from leaving the key hole 128 unless withdrawn axially. In other embodiments, the key hole axis might not be substantially perpendicular to the opening of the passage, however, the fixed alignment between the key hole axis 130 and the cannula 124 means that the cannula will always be facing a known direction relative to an instrument being placed into the key hole 128, thereby helping to ensure that the cannula is aligned with the instrument being placed therein and engaging the key hole 128. This can help facilitate visualization for the surgeon through the cannula to the point where work is being done inside the patient. In this embodiment, the cannula 124 also has some ribbing 132 and is sized to fit within an intercostal space of a patient's rib cage.

FIGS. 5A, 5B, 5C, 5D, 5E, and 5F are front, left, right, back, top, and bottom views, respectively, of the keyhole cannula 124 of FIG. 4.

Figure 6A:
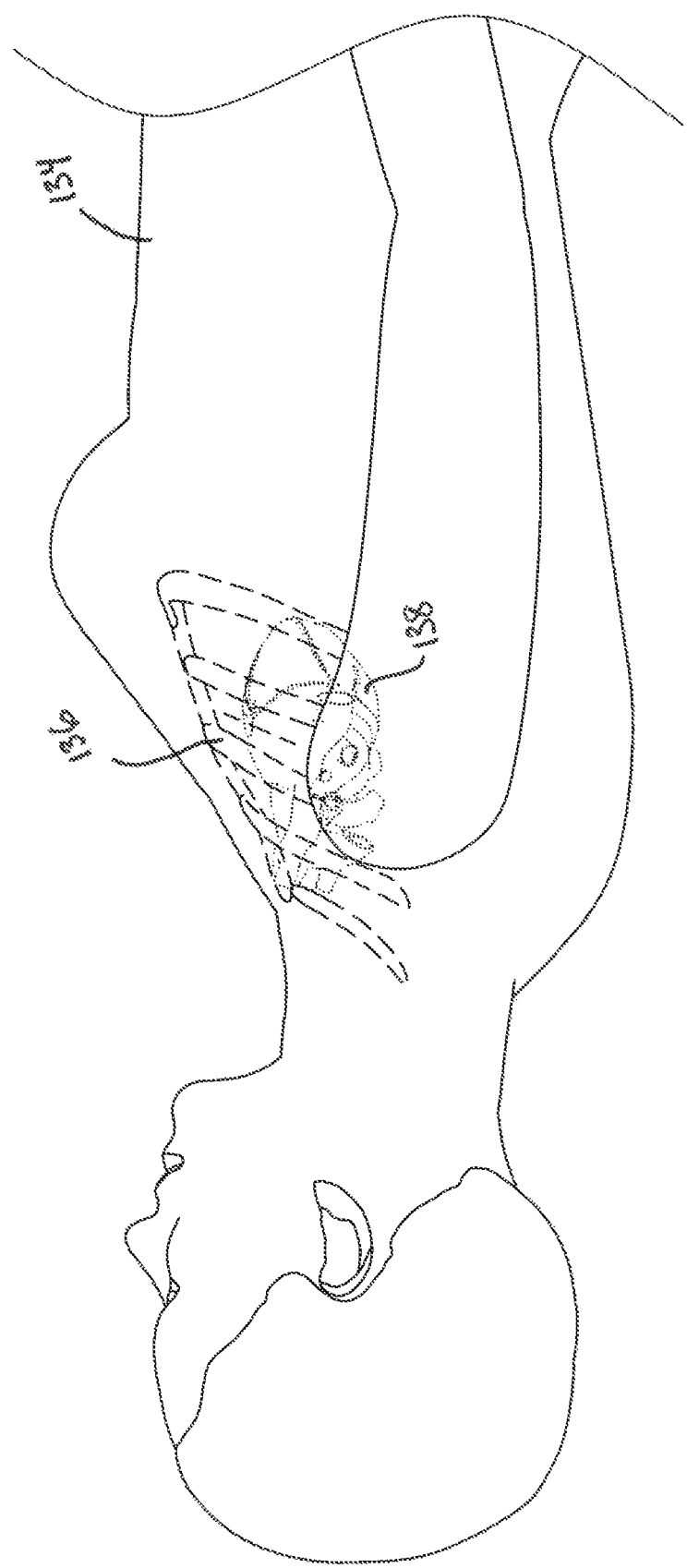
Figure 6B:
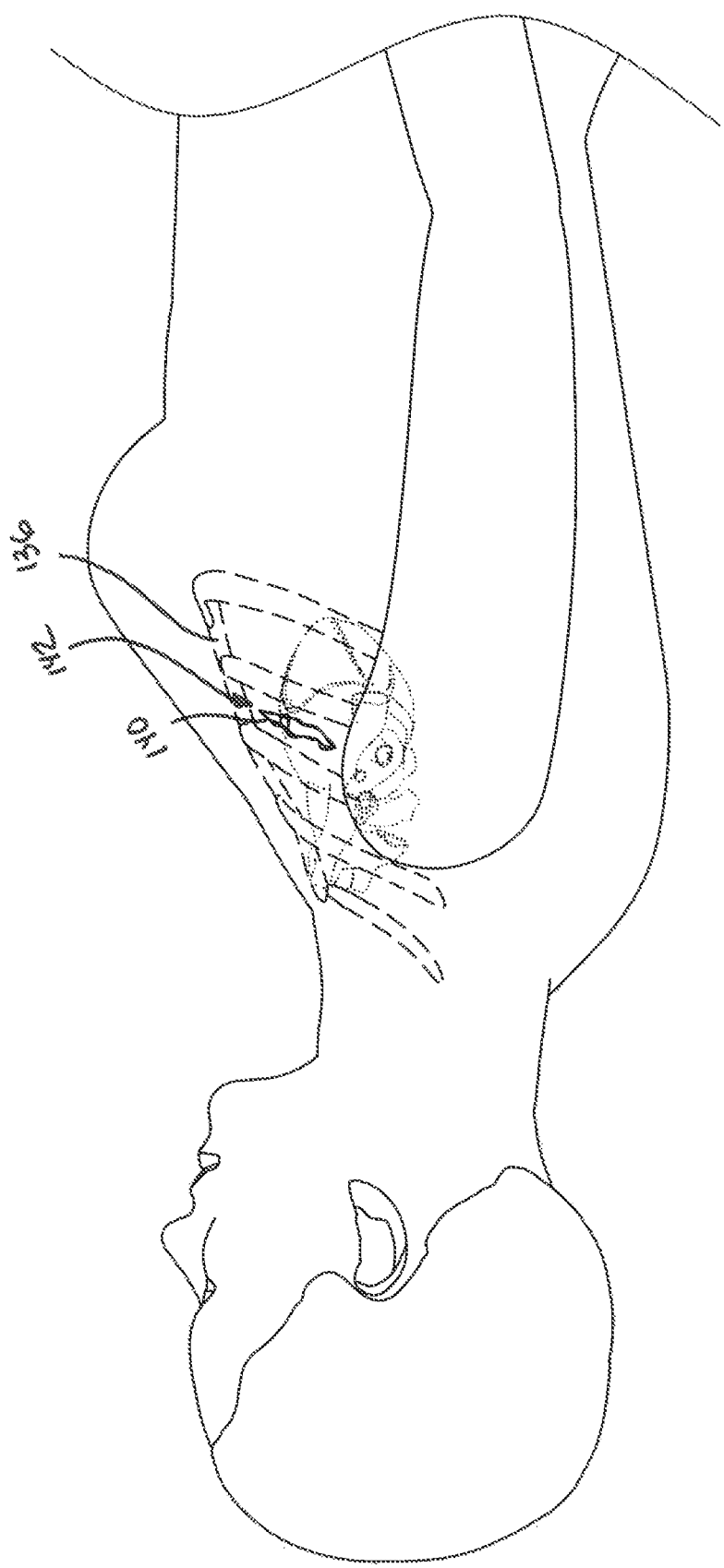
Figure 6C:
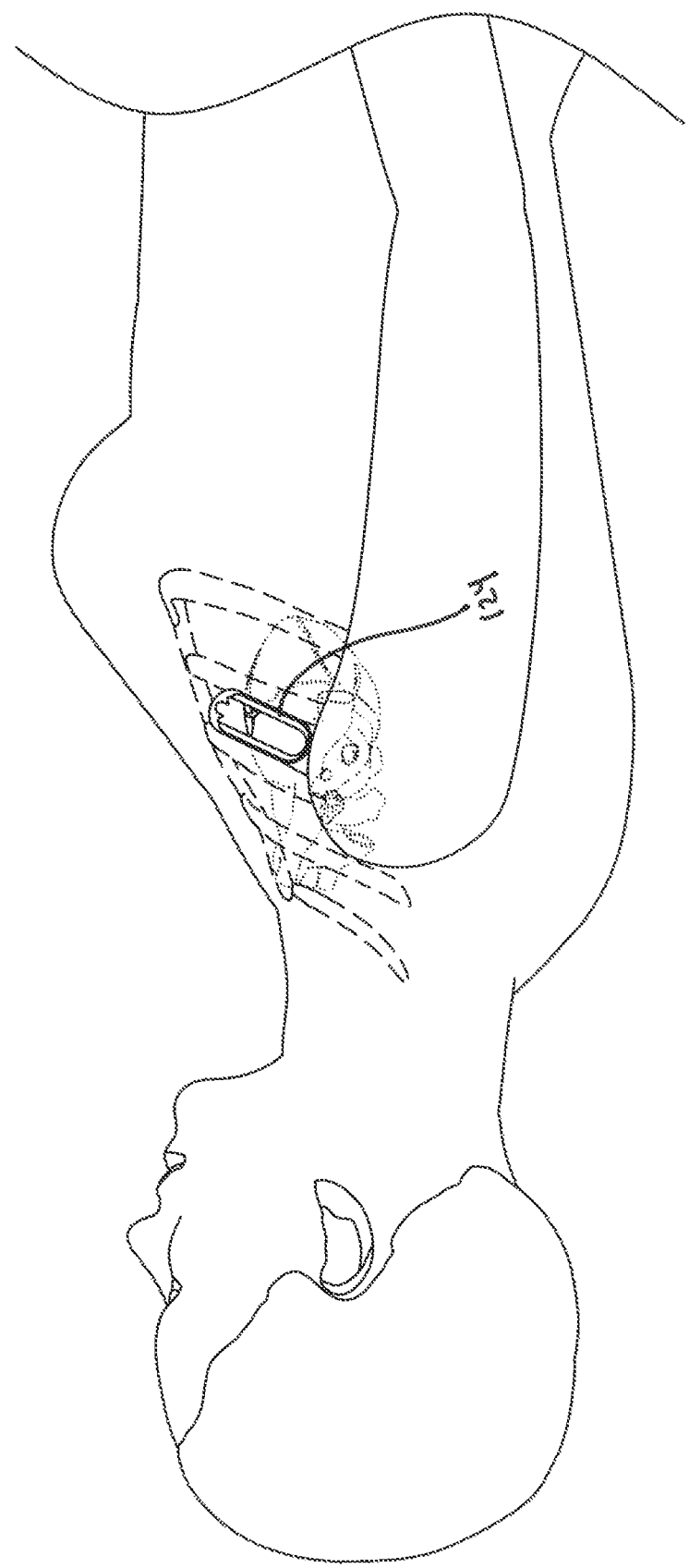
Figure 6D:
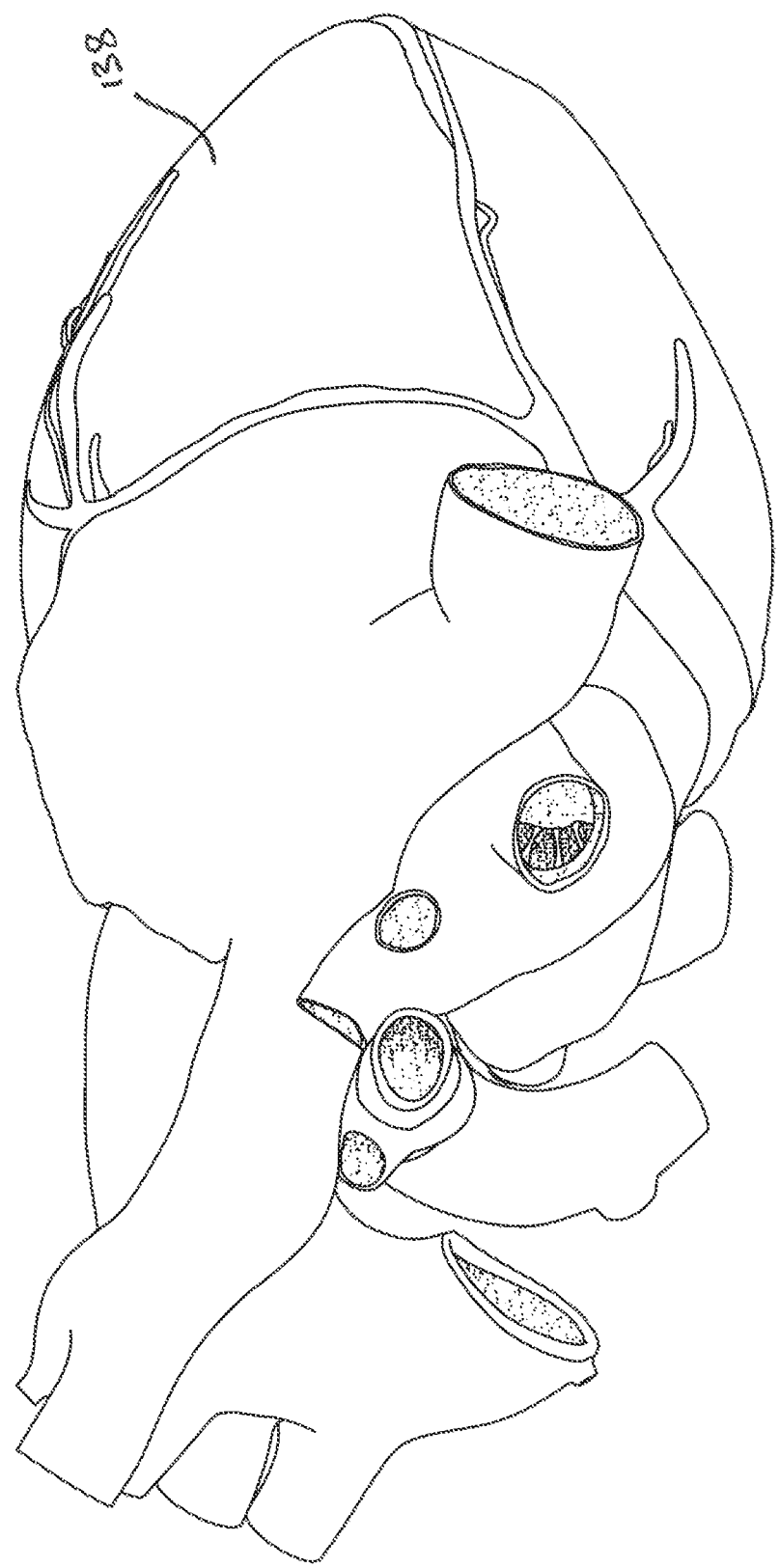
Figure 6E:
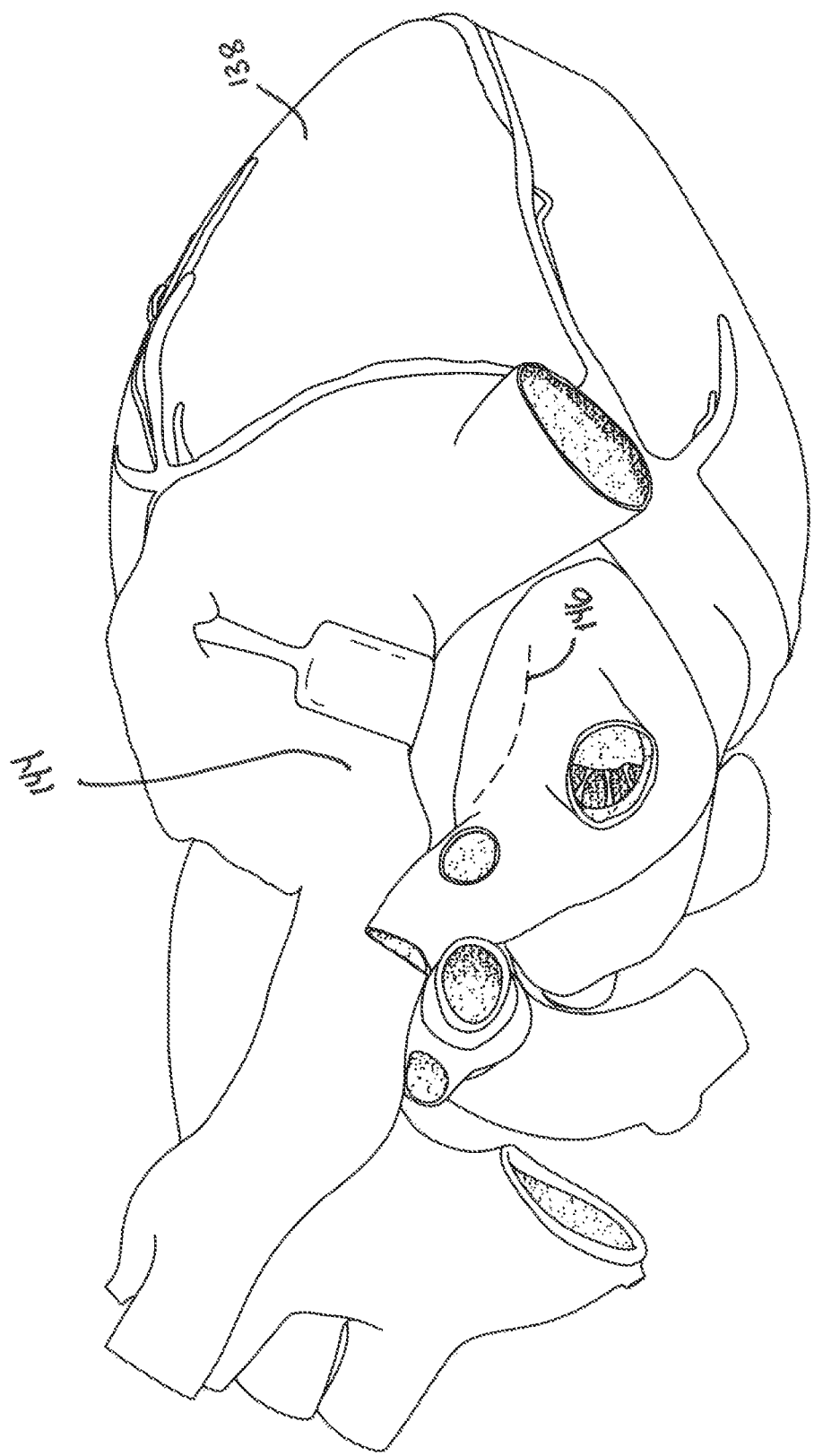
Figure 6F:
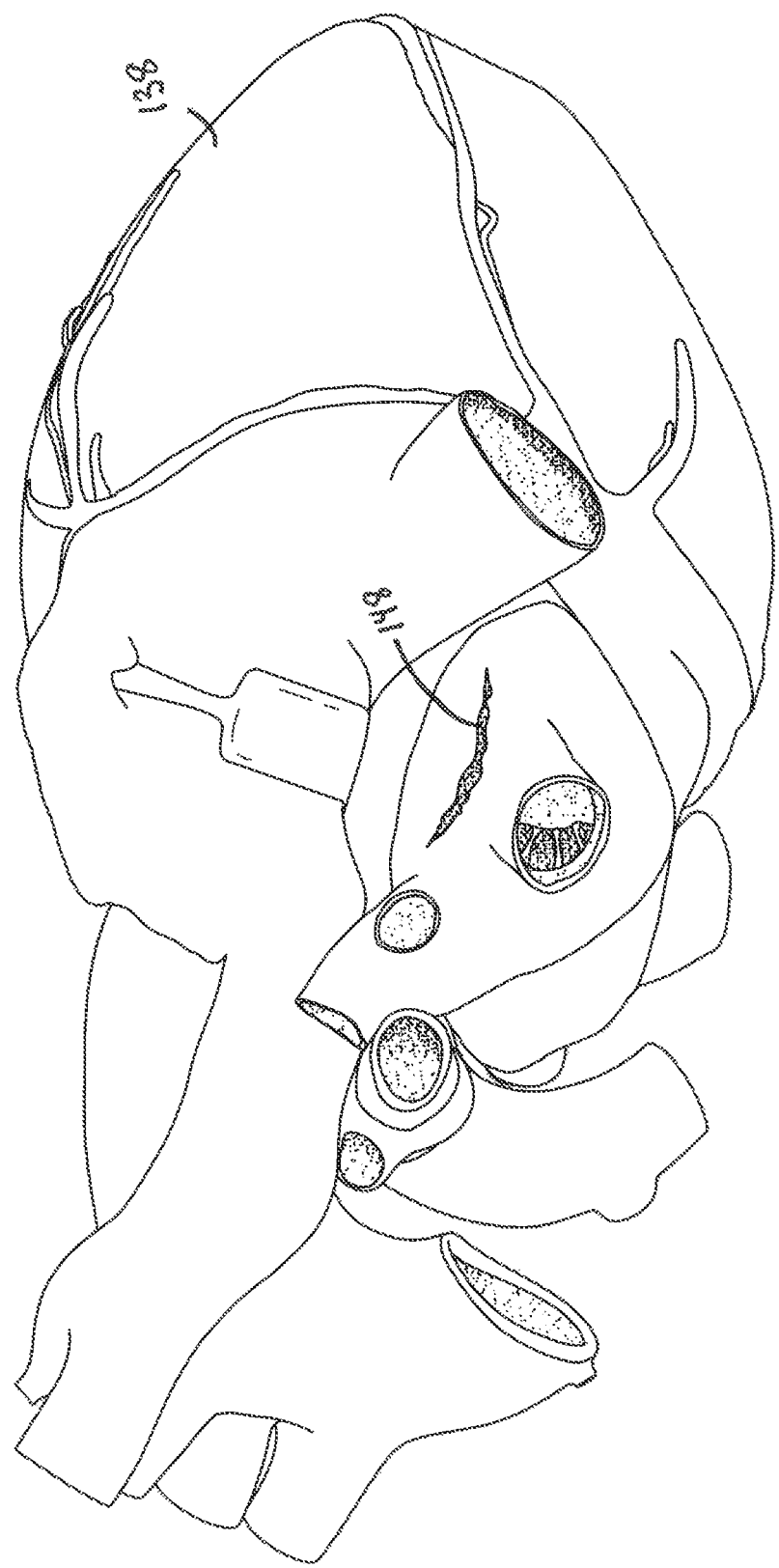

FIGS. 6A-6H, 6J-6N, and 6P-6R illustrate an example of a surgical procedure using the cardiac retractor of FIG. 1 and the keyhole cannula of FIG. 4. FIG. 6A illustrates a patient 134 with a portion of their ribcage 136 visible, and their heart 138 within the thoracic cavity. As shown in FIG. 6B, an incision 140 is made in an intercostal space 142 of the rib cage 136. As shown in FIG. 6C, a keyhole cannula 124 may be placed within the intercostal incision 140. The long outer sides of the cannula 124 are smooth and do not have ribbing in order to avoid traumatizing nerves and vessels which may run along the adjacent ribs. FIG. 6D is an enlarged schematic view of the heart 138, such as a surgeon might see when looking through the cannula 124. As shown in FIG. 6E, vessels 144 may be manipulated to locate a desired incision point 146 on the wall of the heart 138. As shown in FIG. 6F, an incision 148 may be made in the wall of the heart 148 at the desired location. In this example, the incision 148 has been made into the left atrium of the heart 138.

Figure 6G:
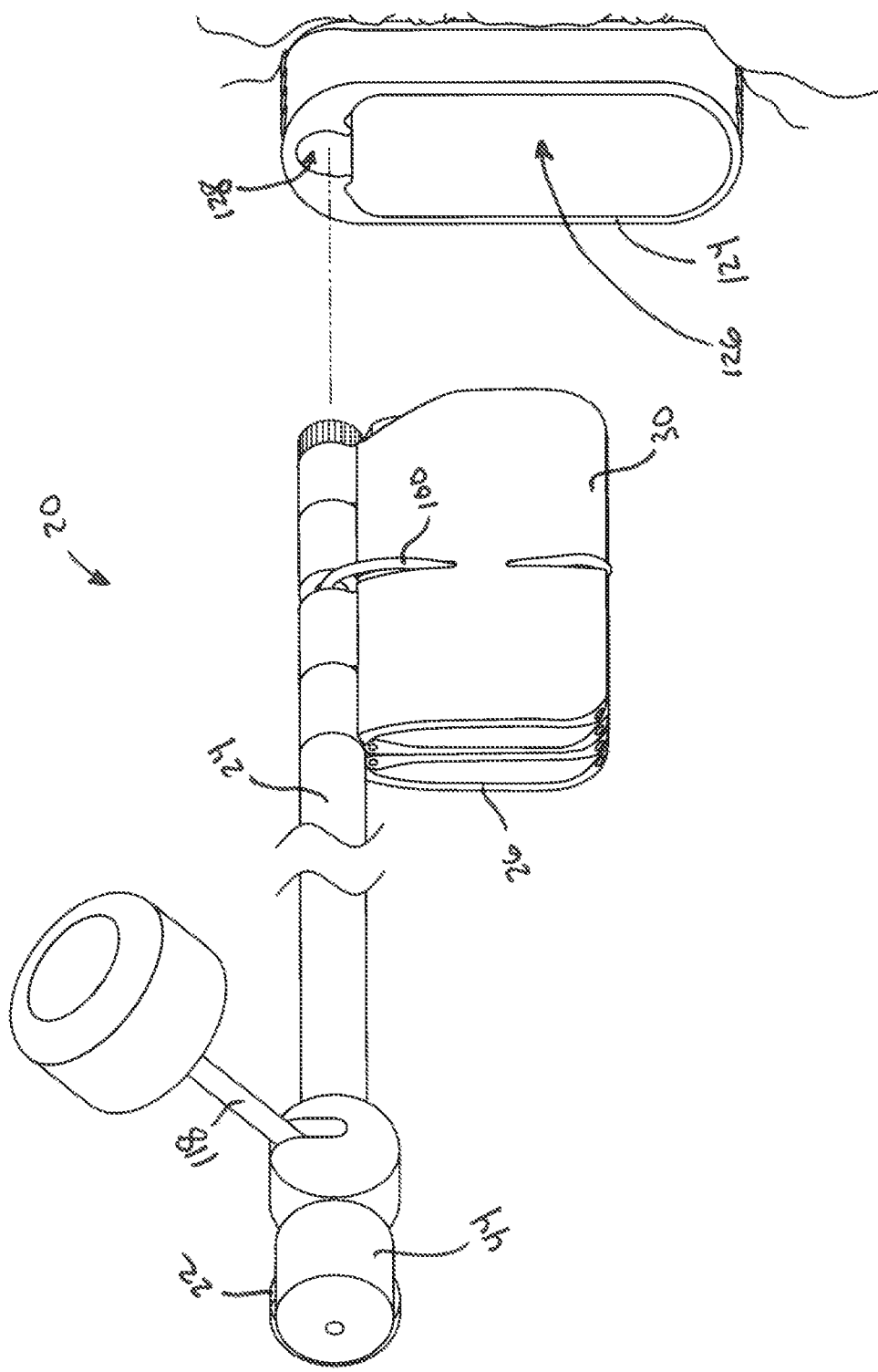
Figure 6H:
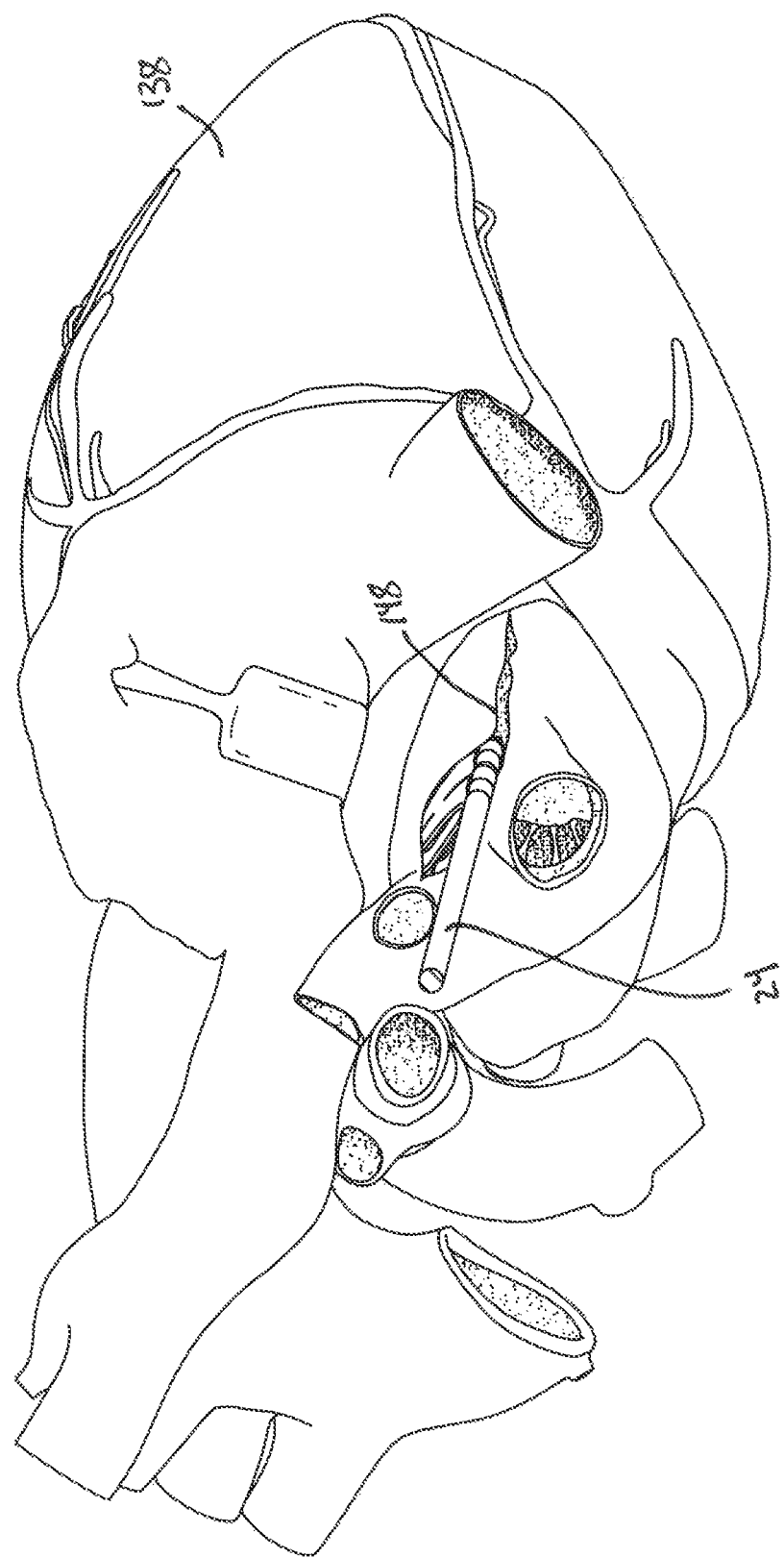
Figure 6J:
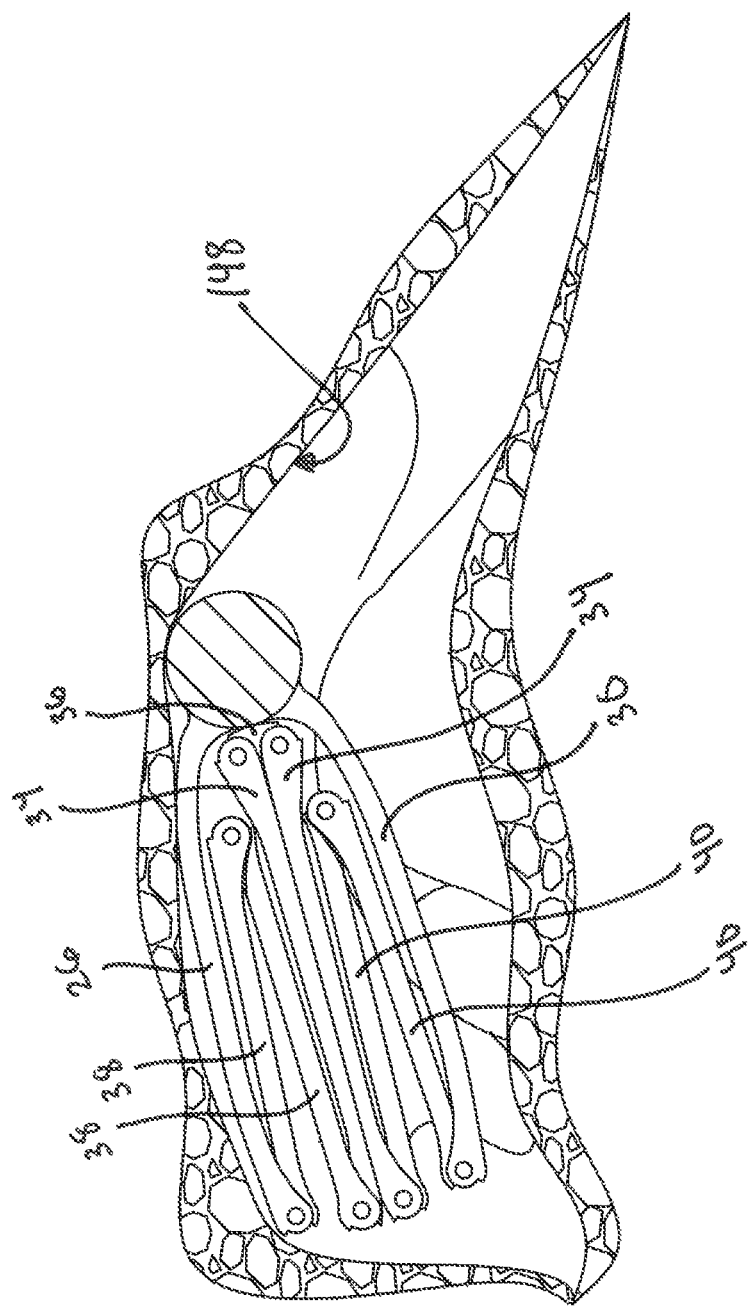
Figure 6M:
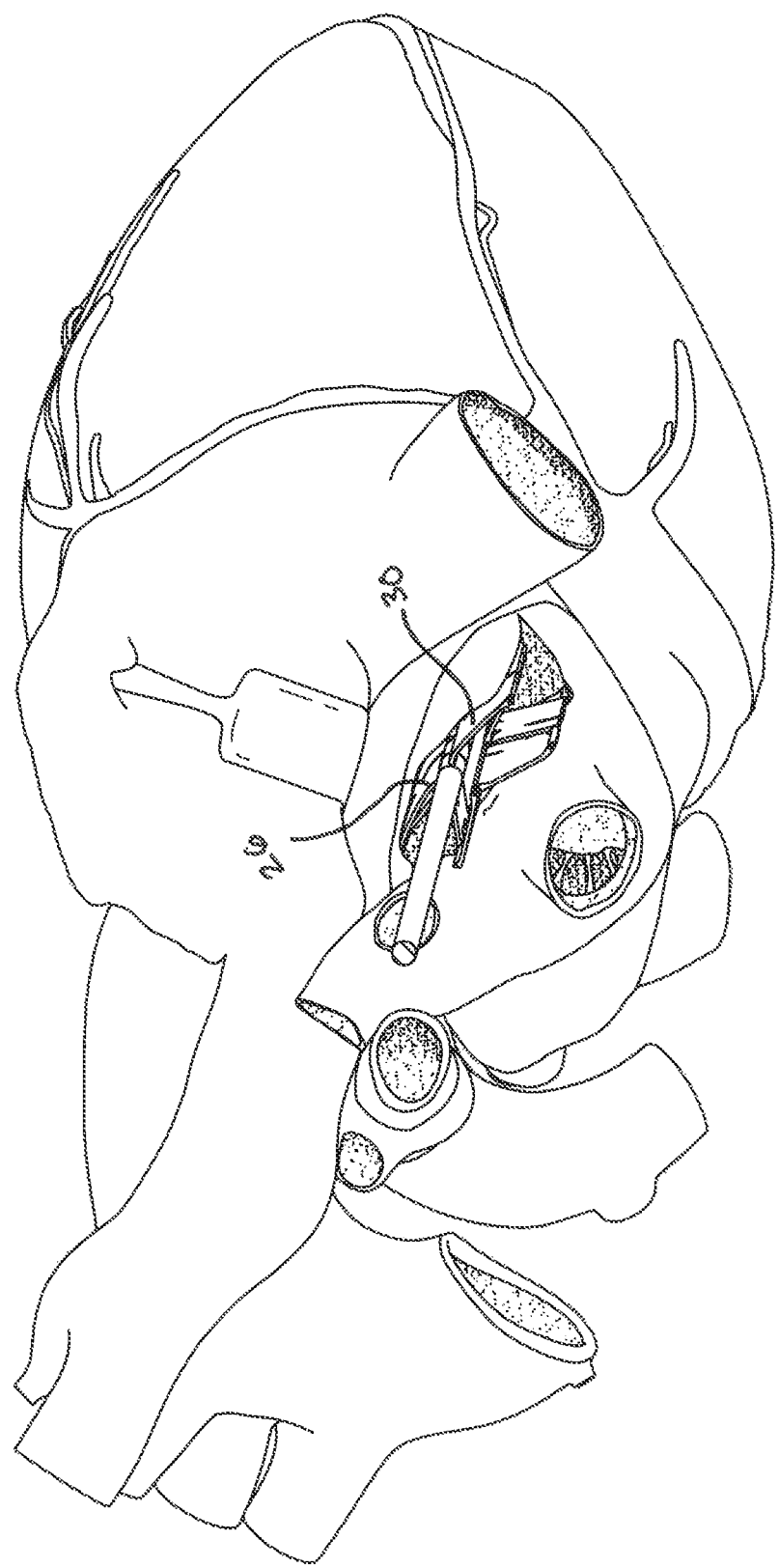
Figure 6N:
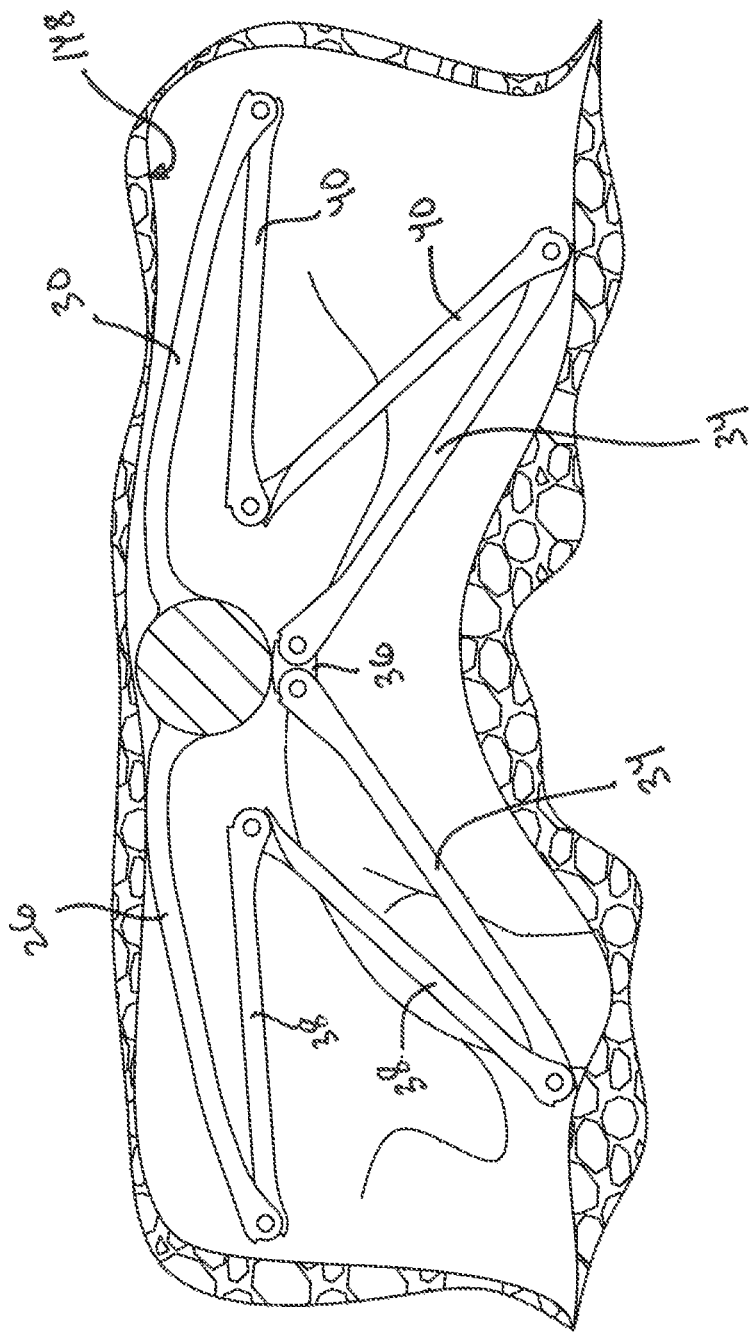

FIG. 6G refocuses on the outside of the patient. The cardiac retractor 20 having its fixed key 118 is rotated out of the fixed collar 22 so that the keyed link 30 is rotated down towards the fixed link 26, and with the other links folded therebetween because tension has not been applied to the deployment cable 100 by the tension knob 44 is inserted into the keyhole 128 of the keyhole cannula 124. The folded links 26, 30 fit within the cannula passage 126, while the keyhole 128 is sized to hold the outer tube 24. Once the links have passed through the cannula, the outer tube 24 can be rotated within the cannula 124 to orient the folded links as desired. As shown in FIG. 6H, looking back at the heart 138 again, the folded links have been rotated to align with the incision 148. This is shown in a schematic elevational view of FIG. 6J, where the folded links 26, 38, 38, 34, 36, 34, 40, 40, and 30 can be seen in a closed or undeployed configuration. For simplicity, the deployment cable is not shown in this view.

As shown in FIG. 6K, outside the patient again, the fixed key 118 is then rotated into alignment with the fixed collar 22, and then, as shown in FIG. 6L, the coaxial nut 28 is threaded into onto threads within the fixed collar 22 to hold the fixed key 118 in this deployed position. Inside the patient, this rotation of the fixed key 118 into alignment with the fixed collar 22 results in the keyed link 30 pivoting to the open/deployed position relative to the fixed link 26 as shown in the perspective view of FIG. 6M and the schematic elevational view of FIG. 6N.

Figure 6P:
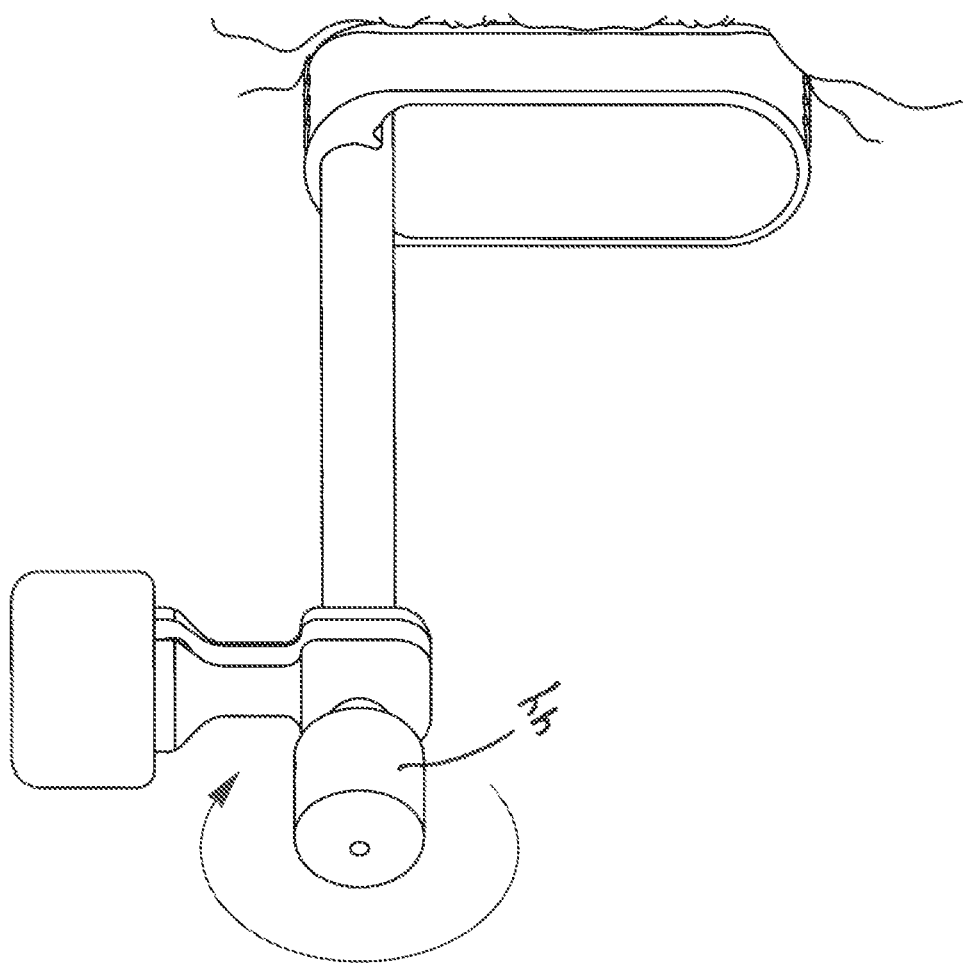
Figure 6Q:
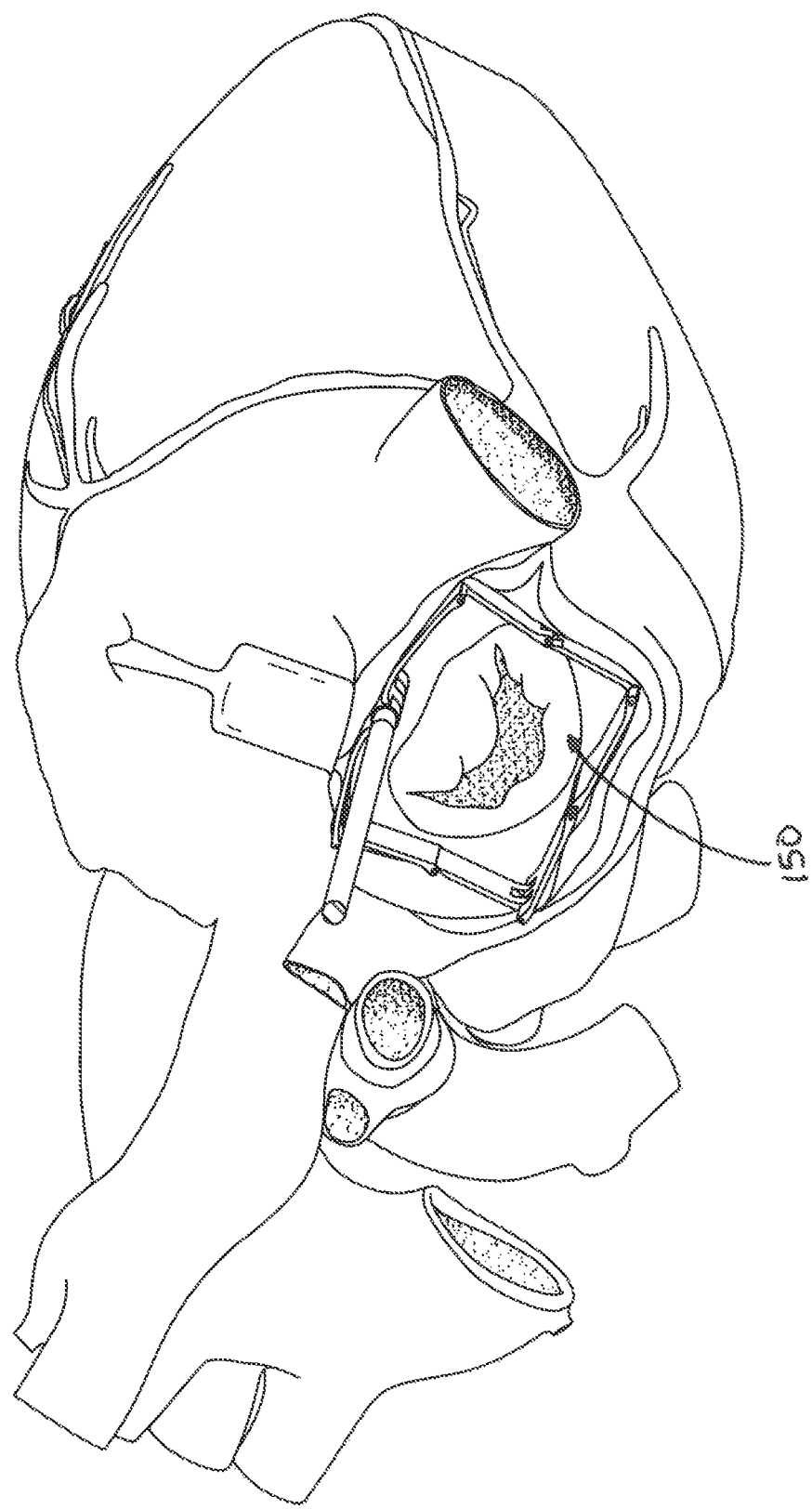

FIG. 6P refocuses outside the patient again. The tension knob 44 is tightened, drawing the tension nut 106 proximally towards the user, and applying tension to the deployment cable 100. This causes the links 38, 38, 34, 36, 36, 40, and 40 to create an opening 150, visible in the inside-patient-views of FIGS. 6Q and 6R, which effectively retracts the wall of the heart, allowing for surgical access. For simplicity, the deployment suture is not shown in FIG. 6Q, however, the tensioned deployment cable is shown schematically in FIG. 6R.

Figure 7:
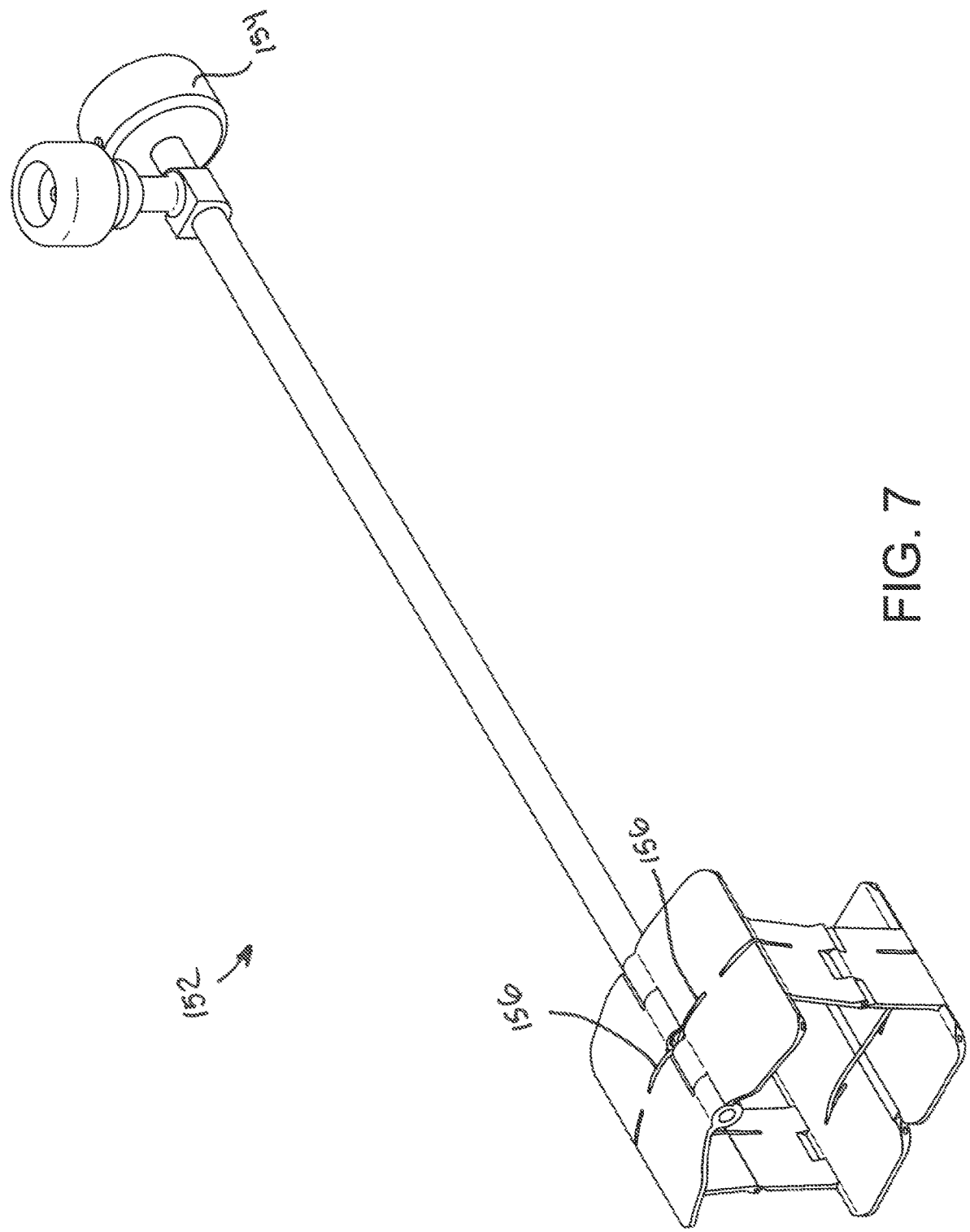
FIG. 7 is a perspective view of another embodiment of a cardiac retractor.
Figure 8A:
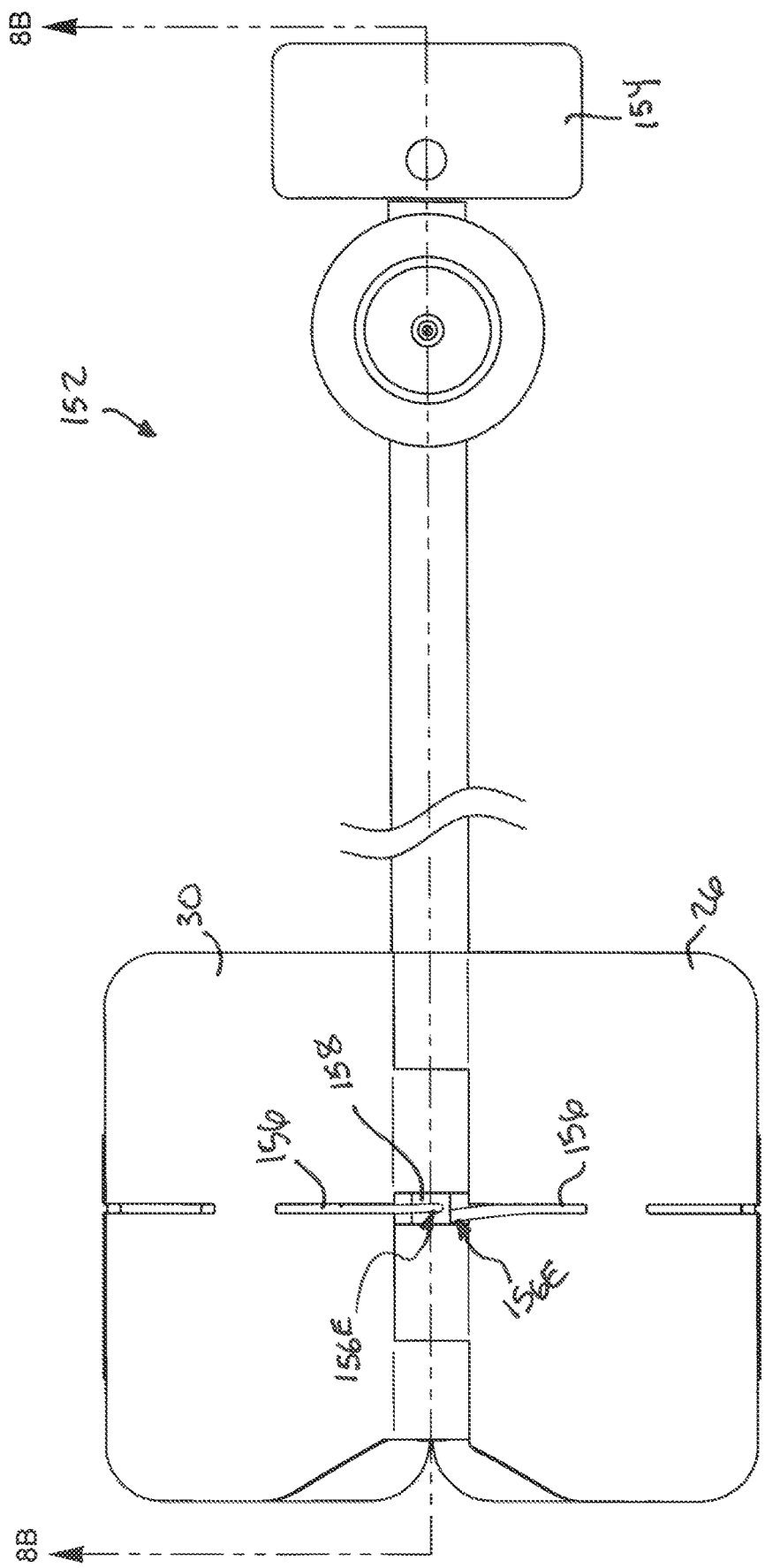
FIG. 8A is a top view of the cardiac retractor of FIG. 7 showing cross-section line 8B-8B.
Figure 8B:
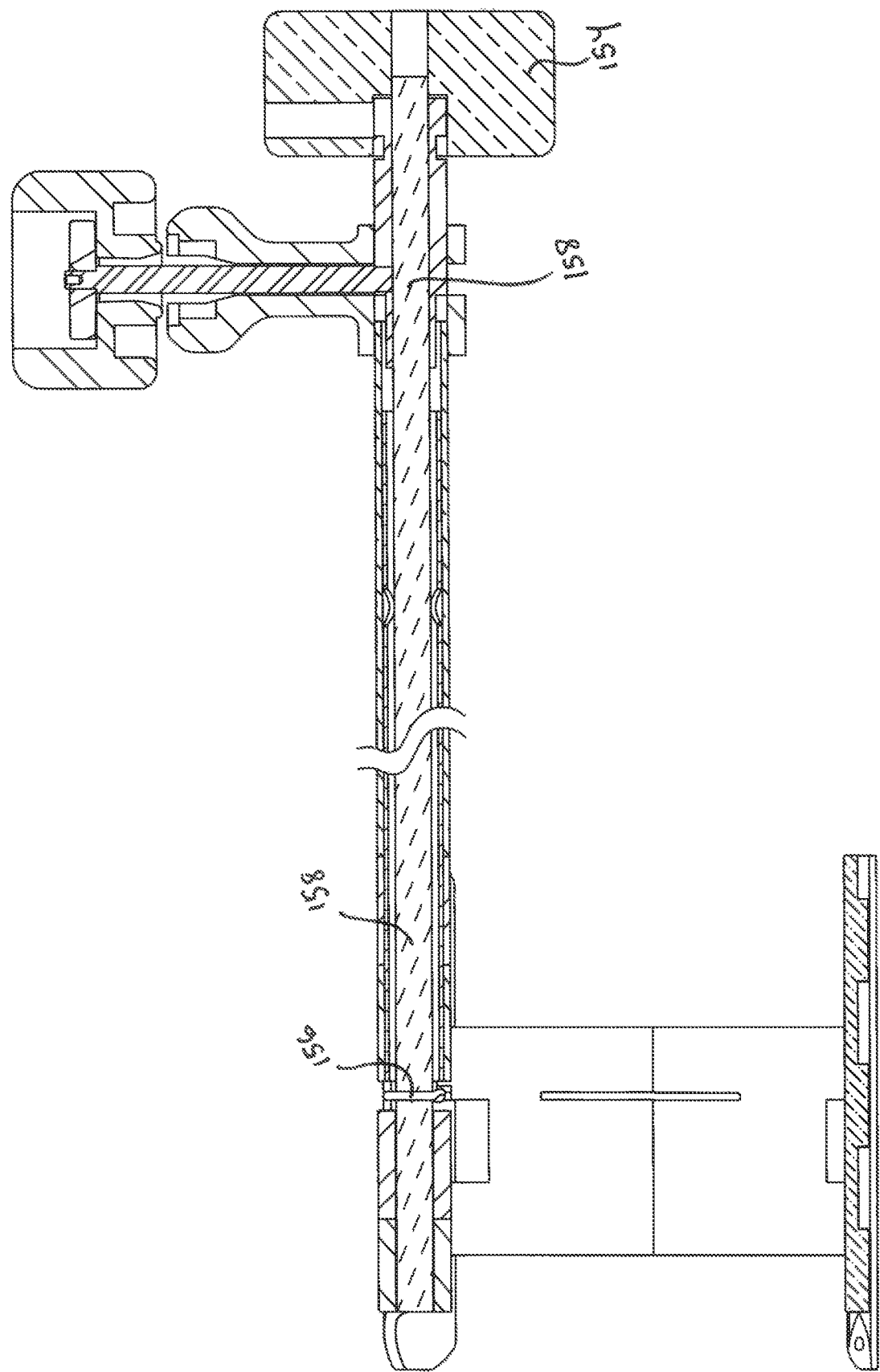
FIG. 8B is a side cross-sectional view of the cardiac retractor of FIG. 8A.

FIG. 7 is a perspective view of another embodiment of a cardiac retractor 152. This embodiment is similar to the previous embodiment, except that the tension knob 154 is coupled to the deployment cable 156 in a different manner. FIG. 8A is a top view of the cardiac retractor 152 of FIG. 7 showing cross-section line 8B-8B. In this view, it can be seen that the ends 156E of the deployment cable 156 are coupled directly to a tension rod 158 which passes within the fixed and keyed links 26, 30. The tension rod 158 is directly coupled to the tension knob 154 such that rotation of the tension knob 154 rotates the tension rod 158, thereby either drawing in or letting out the deployment cable 156. FIG. 8B is a side cross-sectional view of the cardiac retractor of FIG. 8A, taken along line 8B-8B.

Figure 9A:
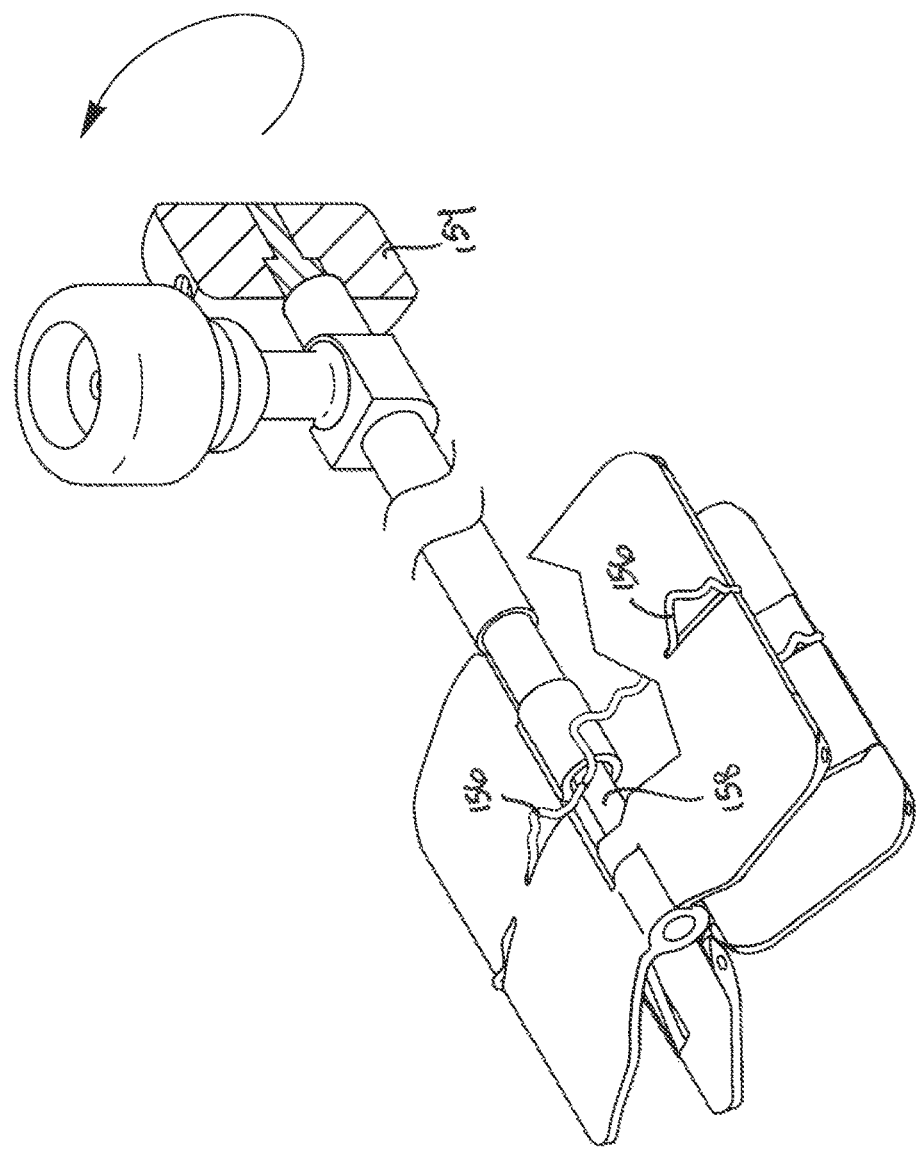

FIGS. 9A and 9B are both partial cross-sectional and partially exposed views which illustrate the deployment cable mechanism for the cardiac retractor embodiment of FIG. 7. In FIG. 9A, the tension knob 154 has been loosed, meaning the folded links are not caused to be deployed. In FIG. 9B, the tension knob has been tightened, causing the deployment cable 156 to wrap around the tension rod 158, thereby causing the deployment cable 156 to open the links 38, 38, 34, 36, 34, 40, and 40.

Various advantages of a cardiac retractor have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A cardiac retractor, comprising:
   an outer tube;
   a fixed collar fixedly coupled to a proximal end of the outer tube;
   a fixed link fixedly coupled to a distal end of the outer tube;
   an inner tube rotatable within the outer tube;
   a fixed key coupled to a proximal end of the inner tube and configured to rotate the inner tube relative to the outer tube;
   a keyed link coupled to a distal end of the outer tube; and
   a first set of side links pivotably coupled to each other;
   a second set of side links pivotably coupled to each other;
   a set of opposing links pivotably coupled to each other; and
   wherein:
      the first set of side links is pivotably coupled between the fixed link and the opposing links; and
      the second set of side links is pivotably coupled between the keyed link and the opposing links.

2. The cardiac retractor of claim 1, further comprising a coaxial nut slideably coupled to the fixed key and configured to secure the fixed key relative to the fixed collar.

3. The cardiac retractor of claim 1, further comprising a key mount collar for coupling the fixed key to the inner tube.

4. The cardiac retractor of claim 1, further comprising:
   a tension nut slideable within the inner tube; and
   a cable tension knob coupled to the tension nut for sliding the tension nut proximally and distally within the inner tube.

5. The cardiac retractor of claim 4, further comprising a deployment cable coupled to the tension nut and threaded through the keyed link, the fixed link, the side links, and the opposing links.

6. The cardiac retractor of claim 5, wherein the deployment cable is threaded through the keyed link, the fixed link, the side links, and the opposing links such that proximal movement of the tension nut within the inner tube causes the links to move to a deployed position.

* * * * *